United States Patent
Vicari et al.

(10) Patent No.: US 12,297,167 B2
(45) Date of Patent: May 13, 2025

(54) PROCESS FOR PREPARING METHANOL FROM CARBON DIOXIDE AND HYDROGEN WITH QUANTITATIVE CARBON DIOXIDE UTILIZATION

(71) Applicant: BASF SE, Ludwigshafen am Rhein (DE)

(72) Inventors: Maximilian Vicari, Ludwigshafen am Rhein (DE); Susanne Britzius, Ludwigshafen am Rhein (DE); Sven Reining, Ludwigshafen am Rhein (DE); Torsten Katz, Ludwigshafen am Rhein (DE); Thomas Geiger, Ludwigshafen am Rhein (DE); Gerald Meyer, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 424 days.

(21) Appl. No.: 17/793,668

(22) PCT Filed: Jan. 11, 2021

(86) PCT No.: PCT/EP2021/050340
§ 371 (c)(1),
(2) Date: Jul. 19, 2022

(87) PCT Pub. No.: WO2021/148262
PCT Pub. Date: Jul. 29, 2021

(65) Prior Publication Data
US 2023/0101490 A1    Mar. 30, 2023

(30) Foreign Application Priority Data
Jan. 22, 2020 (EP) .................................. 20153141

(51) Int. Cl.
*C07C 29/151*    (2006.01)
*C07C 29/154*    (2006.01)
*C07C 31/04*    (2006.01)

(52) U.S. Cl.
CPC ........ *C07C 29/1518* (2013.01); *C07C 29/154* (2013.01); *C07C 31/04* (2013.01)

(58) Field of Classification Search
CPC ... C07C 29/1518; C07C 29/154; C07C 31/04; Y02P 20/129
See application file for complete search history.

(56) References Cited

U.S. PATENT DOCUMENTS

2008/0236390 A1    10/2008    Anders et al.
2010/0192770 A1    8/2010     Andarcia et al.
(Continued)

FOREIGN PATENT DOCUMENTS

EP    1762555 A1    3/2007
WO    2020/048809 A1    3/2020

OTHER PUBLICATIONS

Haag et al., "How to Convert CO2 to Green Methanol," Challenges for Petrochemicals and Fuels: Integration of Value Chains and Energy Transition, DGMK Conference, Oct. 12, 2018, pp. 59-67.
(Continued)

*Primary Examiner* — Jafar F Parsa
(74) *Attorney, Agent, or Firm* — Faegre Drinker Biddle & Reath LLP

(57) ABSTRACT

A process for preparing methanol from carbon dioxide and hydrogen in a methanol synthesis unit and working up the reaction mixture obtained stepwise to isolate the methanol, wherein the carbon dioxide, carbon monoxide, dimethyl ether and methane components of value from the streams
(Continued)

separated off in the isolation of the methanol from the methanol reaction stream are combusted with an oxygenous gas, and the carbon dioxide in the resultant flue gas is separated off in a carbon dioxide recovery unit and recycled to the methanol synthesis unit.

15 Claims, 6 Drawing Sheets

(56) References Cited

U.S. PATENT DOCUMENTS

| | | |
|---|---|---|
| 2011/0094381 A1 | 4/2011 | Lichtfers et al. |
| 2019/0185396 A1 | 6/2019 | Schulz et al. |

OTHER PUBLICATIONS

International Search Report and Written Opinion received for PCT Patent Application No. PCT/EP2021/050340, mailed on Apr. 19, 2021, 10 pages.
Ott et al., "Chapter: 4.2. Catalysts", Methanol, Ullmann's Encyclopedia of Industrial Chemistry, 2012, pp. 6-7.
Ott et al., "Chapter: 5.2.1. Reactor Design", Methanol, Ullmann's Encyclopedia of Industrial Chemistry, 2012, pp. 10-11.
Ott et al., "Chapter: 5.2.2 Large-Scale Methanol Synthesis Loop Designs", Methanol, Ullmann's Encyclopedia of Industrial Chemistry, 2012, pp. 11-12.
Ott et al., "Chapter: 5.3.1 CO2-to-Methanol", Methanol, Ullmann's Encyclopedia of Industrial Chemistry, Oct. 15, 2012, pp. 12-13.
Reddy et al., "Cost effective CO2 capture from flue gas for increasing methanol plant production", Energy Procedia, vol. 63, 2014, pp. 1407-1414.
Rompp, "Rompp Lexikon Chemie - Methanisierung", 2019, 1 page.
Topham et al., "Chapter: 13.3 CCS-related Separation Technologies", Carbon Dioxide, Ullmann's Encyclopedia of Industrial Chemistry, 2014, p. 27.

Fig.1 Block diagram (inventive)

PROCESS FOR PREPARING METHANOL FROM CARBON DIOXIDE AND HYDROGEN WITH QUANTITATIVE CARBON DIOXIDE UTILIZATION

CROSS-REFERENCE TO RELATED APPLICATIONS

This application is a national stage application (under 35 U.S.C. § 371) of PCT/EP2021/050340, filed Jan. 11, 2021, which claims benefit of European Application No. 20153141.5, filed Jan. 22, 2020, both of which are incorporated herein by reference in their entirety.

The present invention relates to a process for preparing methanol from carbon dioxide and hydrogen, in which the carbon compounds in the streams separated off in the synthesis and isolation of the methanol, are converted to carbon dioxide and, with avoidance of emission thereof, and reused in the preparation of methanol. This process is based on the continuously operated methanol synthesis, known to those skilled in the art, by the low-pressure process.

Methanol is one of the most important synthesis raw materials globally and its uses include not only its use as solvent but also for the syntheses of formaldehyde, acetic acid, methyl tert-butyl ether (MTBE), dimethyl terephthalate, methyl methacrylate and methylamines in large volumes.

Methanol is produced on the industrial scale from synthesis gas in a reactor in the presence of a methanol synthesis catalyst. The synthesis gas comprises mainly hydrogen and carbon monoxide, and, depending on the amount of production and workup, also corresponding amounts of carbon dioxide, water and what are called inert gases, for instance methane, nitrogen or argon.

According to Ullmann's Encyclopedia of Industrial Chemistry, "Methanol" chapter, 2012 Wiley-VCH Verlag GmbH & Co. KGaA, Weinheim, Germany, synthesis gas is converted to methanol typically in what is called the low-pressure process within a pressure range of 5 to 10 MPa over copper- and zinc-comprising methanol synthesis catalysts. This involves converting both carbon monoxide and carbon dioxide to methanol.

$$CO+2H_2 \rightleftharpoons CH_3OH \qquad (1)$$

$$CO_2+3H_2 \rightleftharpoons CH_3OH+H_2O \qquad (2)$$

In addition to the two methanol-forming reactions (1) and (2), the endothermic reverse water-gas shift reaction of carbon dioxide and hydrogen has also to be taken into account.

$$CO_2+H_2 \rightleftharpoons CO+H_2 \qquad (3)$$

As a side reaction, methanation of carbon monoxide and carbon dioxide occurs under these reaction conditions, as it is for example described in Römpp Lexikon Chemie, "Methanisierung", 2019, Georg Thieme Verlag K G, Stuttgart.

$$CO+3H_2 \rightleftharpoons CH_4+H_2O \qquad (4)$$

$$CO_2+4H_2 \rightleftharpoons CH_4+2H_2O \qquad (5)$$

Based on reaction equations (1) and (2), the stoichiometric number S is found as follows for the methanol synthesis:

$$S = \frac{n(H_2) - n(CO_2)}{n(CO) + n(CO_2)} \qquad (6)$$

where n in each case represents the respective molar amounts. A stoichiometric number S of 2 corresponds to the theoretical number. Since, however, a deficit of hydrogen significantly reduces the selectivity for methanol, a stoichiometric number S of slightly above 2 is considered to be the optimum for methanol synthesis.

The synthesis gas which is normally used in the classical methanol synthesis is typically obtained from natural gas, other streams comprising hydrocarbons and in some cases also by coal gasification or wood gasification. Standard preparation processes are steam reforming, autothermal reforming, combinations thereof or partial oxidation. All these processes require a valuable carbon source and energy for their conversion to synthesis gas. Such energy is typically generated by the burning of a fossil fuel like natural gas. Thus, already the classical production of synthesis gas generates carbon dioxide as a byproduct of the energy production.

In the classical methanol synthesis as described for the Lurgi MegaMethanol in Ullmann's Encyclopedia of Industrial Chemistry, "Methanol" chapter, section 5.2.2, 2012 Wiley-VCH Verlag GmbH & Co. KGaA, Weinheim, Germany, synthesis gas is converted under heterogeneous catalysis to methanol in a methanol synthesis reactor and a methanol-enriched crude methanol stream is first condensed out of the reaction mixture obtained. The remaining gas stream comprises unconverted hydrogen inter alia, and is sent to a pressure swing adsorption for recovery thereof. The hydrogen thus recovered is recycled to the methanol synthesis. The gas stream not absorbed in the pressure swing adsorption is finally sent to thermal utilization. The methanol-enriched liquid stream obtained by the abovementioned condensing-out is subsequently expanded for outgassing and the expansion gas is likewise sent to thermal utilization. The further methanol-enriched liquid stream that remains after the outgassing is then subjected to a multistage distillation for the actual methanol recovery. In this case, the off-gas stream from the low boiler column is also sent to thermal utilization.

Although unconverted hydrogen is removed and recycled to the methanol synthesis, all other gases of value, after they have been separated off, are merely sent to a thermal utilization. Thus, the unconverted carbon dioxide and carbon monoxide also remain unutilized for further recovery of methanol. Even though these remain unutilized for further methanol recovery, the volume flows thereof should, however, be taken into account in the design of the plant, for instance in the form of the required apparatus dimensions for handling of the volume flows. Furthermore, the handling of these volume flows does of course also require energy, for instance in the form of heating, compression or pumping energy, without these being utilized for further methanol synthesis. Moreover, the thermal utilization of the gases of value leads to a further increase in carbon dioxide emission. Combustible gases, which also include carbon monoxide, are converted to carbon dioxide. The carbon dioxide itself that is already present is passed through the thermal utilization unchanged.

In summary, both, the classical production of synthesis gas as well as the classical methanol synthesis convert only a part of the carbon of the used carbonaceous source into methanol and further more produce carbon dioxide containing off-gases. This was already recognized in the state of the art and various improvements to increase the degree of carbon utilization and to decrease the amount of carbon dioxide containing off-gases developed.

S. Reddy et al. in Energy Procedia 63 (2014) 1407-1414 likewise suggests utilizing carbon dioxide from synthesis gas production or from carbon dioxide-containing streams from methanol synthesis for further methanol synthesis. Specifically, the publication teaches absorbing the carbon dioxide from the flue gas from the synthesis gas reformer in an aminic solvent by means of an "Econamine FG Pluss$^{SM}$" gas scrubbing unit, then releasing it again as a carbon dioxide stream and feeding this carbon dioxide stream either together with the feed gas stream to the reformer for production of the synthesis gas or feeding it directly straight to the synthesis gas. Moreover, the publication teaches returning what are called purge gases and off-gases from the workup of the methanol stream directly to the compression stage upstream of the methanol synthesis reactor and/or feeding them to the reformer as fuel gas. In both cases, the carbon dioxide present therein is fed back to the methanol synthesis. The measures described are said to enable an increase in methanol capacity of about 20%.

In the case of this process too, the direct recycling of purge gases and off-gases to the methanol synthesis reactor is disadvantageous since this results in accumulation of inert gases, for instance nitrogen and argon, but also methane or by-products such as dimethyl ether, in the synthesis circuit. In the variant in which the gas streams mentioned are fed to the fuel gas to the reformer, accumulation of inert gases and by-products is counteracted, but the additional amount of gas means that the reformer has to have a correspondingly large design. The carbon dioxide recovery from the flue gas from the reformer additionally requires a gas scrubbing unit of correspondingly large dimensions, including the incorporation thereof for energy purposes into the overall complex.

PCT/EP 2019/072,713 describes a process for the production of methanol from synthesis gas in which the carbon compounds in the streams separated off in the isolation of the methanol are converted to carbon dioxide and, with avoidance of emission thereof, reused in the preparation of methanol. The streams separated off are fed to a combustion unit in which they are oxidized to carbon dioxide, which is then absorbed in a carbon dioxide recovery unit and after its release recycled back to the synthesis gas production or to the methanol synthesis reactor.

This process is highly efficient and progressive regarding the use of the carbon compounds within the whole methanol synthesis unit. It enables the production of methanol from synthesis gas without emission of carbon dioxide. However, the raw material synthesis unit is generally based on natural gas and the conversion of natural gas into synthesis unit generates carbon dioxide as a byproduct of the required energy production.

The disadvantages of using natural gas to produce synthesis gas have already been discussed in the state of the art and it was realized that methanol can also be produced from carbon dioxide and hydrogen. The technical feasibility of such a so called "$CO_2$-to methanol" process is for instance mentioned in Ullmann's Encyclopedia of Industrial Chemistry, "Methanol" chapter, section 5.3.1, 2012 Wiley-VCH Verlag GmbH & Co. KGaA, Weinheim, Germany.

The use of carbon dioxide plus hydrogen instead of synthesis gas has the benefit that carbon dioxide is often easily available as a by-product or waste material so that only hydrogen has to be produced, whereas for synthesis gas as a basis, the synthesis gas has to be specifically produced from a carbonaceous source like natural gas. Carbon dioxide may, for example, easily come from sources such as fossil based power plants, steal processes, cement industry or chemical production complexes. Hydrogen may, for example, either be available as a surplus in chemical or petrochemical complexes or may be specifically produced, for example by carbon dioxide neutral electrolysis of water.

S. Haag et al. in Challenges for Petrochemicals and Fuels: Integration of Value Chains and Energy Transition, DGMK Conference October 10-12, 2018, Berlin, Germany, describe in their conference proceedings with the title "How to Convert $CO_2$ to Green Methanol" teach and demonstrate by the operation of a pilot plant that even for a fully carbon dioxide and hydrogen based methanol production a standard low pressure process applying a commercially available $Cu/ZnO/Al_2O_3$ methanol catalyst is suitable. They used an interconnection containing a reactor, two separators and a recycle loop. The output of the reactor was fed to the first separator in which not-converted gas was separated off and the methanol containing liquid stream passed on to the second separator in which the raw methanol was separated off. The unconverted gas obtained in the first separator was mainly recycled back to the reactor and a small stream purged out.

Due to its interconnection and operation conditions, the recycle gas in the abovementioned process has a relatively high content of nitrogen inert gas of 2 vol.-%. It decreases des activity of the catalyst and increases the gaseous volume in the process. Moreover, the purge gas mainly contains the valuable educt gases carbon dioxide and hydrogen, which are lost.

The conference proceedings of S. Haag et al. show that also for carbon dioxide and hydrogen as feed, as it is also known from synthesis gas as feed, unconvertible inert gases as typical accompanying impurities, like nitrogen, are normally supplied and tend to enrich in the system.

Another similarity between synthesis gas and carbon dioxide/hydrogen as feed is that even though reaction equations (1), (2) and (3) are equilibrium equations and methanol synthesis catalyst is present, the equilibrium is not established quantitatively.

Therefore, also for the use of carbon dioxide/hydrogen as feed for the production of methanol, the reaction mixture directly after the methanol synthesis typically contains only about 3 to 15 wt.-% of methanol and not inconsiderable amounts of unconverted hydrogen, carbon dioxide, carbon monoxide, and extraneous gases such as nitrogen or argon. Moreover, the reaction mixture also comprises by-products, for example dimethyl ether or methane. The prior art on the preparation of methanol from synthesis gas describes various processes for workup of the reaction mixture obtained. Central steps are typically the stepwise concentration of the methanol, handling the values-containing gases with maximum efficiency, and the avoidance of accumulation of extraneous gases. Such steps may also be relevant for the carbon dioxide and hydrogen based production of methanol.

However, even if carbon dioxide is used as carbonaceous compound for the production of methanol as described in the state of the art, it is not fully converted to methanol so that a part of it is still discharged and typically released to the atmosphere.

It was an object of the present invention to find a process for preparing methanol from carbon dioxide and hydrogen, which has the abovementioned disadvantages only to a minor degree, if at all, and reacts the carbon dioxide virtually completely with hydrogen to give methanol in a carbon dioxide emission-free operation. The process of the invention is to easily use carbon dioxide of different sources and qualities regarding its concentration and possible accompanying compounds. Furthermore, the process of the invention is to be easily performable and is to largely use the apparatuses and interconnections in established methanol synthesis processes customary in the industry and which hitherto have been based on the use of synthesis gas, so that such plants can easily be modified.

A process for preparing methanol has been found, by
(a) converting a carbon dioxide and hydrogen containing stream (I) in a methanol synthesis unit (A) at a temperature of 150 to 300° C. and a pressure of 3 to 10 MPa abs in the presence of a methanol synthesis catalyst to a reaction mixture containing methanol, water, carbon dioxide, carbon monoxide, hydrogen, dimethyl ether and methane, condensing a methanol- and water-enriched crude methanol stream (II) out of said reaction mixture, and conducting the crude methanol stream (II) and a gaseous stream (III) comprising carbon dioxide, carbon monoxide, hydrogen and methane out of the methanol synthesis unit (A),
(b) expanding the crude methanol stream (II) from stage (a) in an expansion unit (B) to a pressure of 0.1 to 2 MPa abs, and obtaining an expansion gas (IV) comprising carbon dioxide and methane and a degassed crude methanol stream (V) enriched with methanol and water,
(c) separating a carbon dioxide- and dimethyl ether-comprising low boiler stream (VI) by distillation from the degassed crude methanol stream (V) from stage (b) in a distillation apparatus (C), and obtaining a methanol- and water-enriched bottom stream (VII), and
(d) separating a water-containing high boiler stream (VIII) from the bottom stream (VII) from stage (c) in a further distillation apparatus (D), and obtaining methanol by distillation as stream (IX), and which comprises
(e) feeding the carbon dioxide, carbon monoxide, dimethyl ether and methane components of value in stream (III) and in at least one of the two streams (IV) and (VI) to a combustion unit (E) and combusting them therein with supply of an oxygenous gas (X) having an oxygen content of 30% to 100 vol.-%, forming carbon dioxide-containing flue gas (XI),
(f) separating a carbon dioxide-enriched stream (XIII) from the carbon dioxide-containing flue gas (XI) from stage (e) in a carbon dioxide recovery unit (F) to form an off-gas stream (XII),
(g) recycling the carbon dioxide-enriched stream (XIII) separated off in the carbon dioxide recovery unit (F) from stage (f) to the methanol synthesis unit (A) of stage (a) as a carbon dioxide containing source of stream (I),
(h) supplying a hydrogen feedstock (XIV) to the carbon dioxide-enriched stream (XIII) to form the carbon dioxide and hydrogen containing stream (I) as a hydrogen containing source of stream (I), and
(i) supplying a carbon dioxide feedstock (XV) to the carbon dioxide-containing flue gas (XI) and/or to the carbon dioxide-enriched stream (XIII) and/or to the carbon dioxide and hydrogen containing stream (I) as a carbon dioxide containing source of stream (I).

The process of the invention is based on the continuously operated methanol synthesis by the low-pressure process known to the person skilled in the art, in which conventionally synthesis gas is converted at a pressure of 3 to 10 MPa abs in the presence of a methanol synthesis catalyst to a methanol-containing reaction mixture and subsequently worked up stepwise for isolation of the methanol. The stepwise workup separates off various streams that still comprise components off value or unconverted feedstocks or by-products, for example carbon dioxide, carbon monoxide, dimethyl ether, methane or further by-products. The core of the invention is the use of carbon dioxide and hydrogen as raw materials instead of synthesis gas and the physical reuse of the carbon of the unconverted feedstocks and by-products of value for further synthesis of methanol with simultaneous avoidance of carbon dioxide emission. The process of the invention is elucidated in detail hereinafter.

BRIEF DESCRIPTION OF THE FIGURES

FIG. 2 is based on FIG. 1 and differs in that the combustion unit (E), as well as a combustion chamber, also comprises a condenser in which water is condensed out of the combustion gas and conducted away as stream (XVI). This distinctly reduces the water content in the flue gas (XI) by a relatively simple measure and facilitates the subsequent recovery of the carbon dioxide.

FIG. 3 is based on FIG. 2 and differs in that, before stream (III) is fed to the combustion unit (E), hydrogen is separated off in a hydrogen recovery unit (G). The hydrogen is preferably removed by pressure swing adsorption. The hydrogen removed is recycled as stream (IIIb) to the methanol synthesis unit (A) and preferably added to the compressor therein.

FIG. 4 is based on FIG. 3 and differs in that the carbon dioxide feedstock (XV) is only supplied to the flue gas stream (XI).

FIG. 5 is based on FIG. 3 and differs in that the carbon dioxide feedstock (XV) is only supplied to the carbon dioxide-enriched stream (XIII). The labels therein have the following meanings:

(A) methanol synthesis unit
(B) expansion unit (low pressure expansion)
(C) low boiler column
(D) pure methanol column
(E) combustion unit
(F) carbon dioxide recovery unit
(G) pressure swing adsorption
(I) carbon dioxide and hydrogen containing stream
(II) methanol-and water-enriched crude methanol
(IIIb) recovered hydrogen from pressure swing adsorption (G)
(III) off-gas from pressure swing adsorption (G)
(IV) expansion gas from expansion unit (B)
(V) degassed crude methanol stream
(VI) low boiler stream from low boiler column (C)
(VII) bottom stream from distillation apparatus (C)
(VIII) high boiler stream from pure methanol column (D)
(IX) pure methanol
(X) oxygenous gas
(XI) flue gas
(XII) off-gas from carbon dioxide recovery unit (F)
(XIII) carbon dioxide-enriched stream from carbon dioxide recovery unit (F)
(XIV) hydrogen feedstock ("fresh hydrogen")
(XV) carbon dioxide feedstock ("fresh carbon dioxide")
(XVI) condensed water from combustion unit (E).

Figure 6:
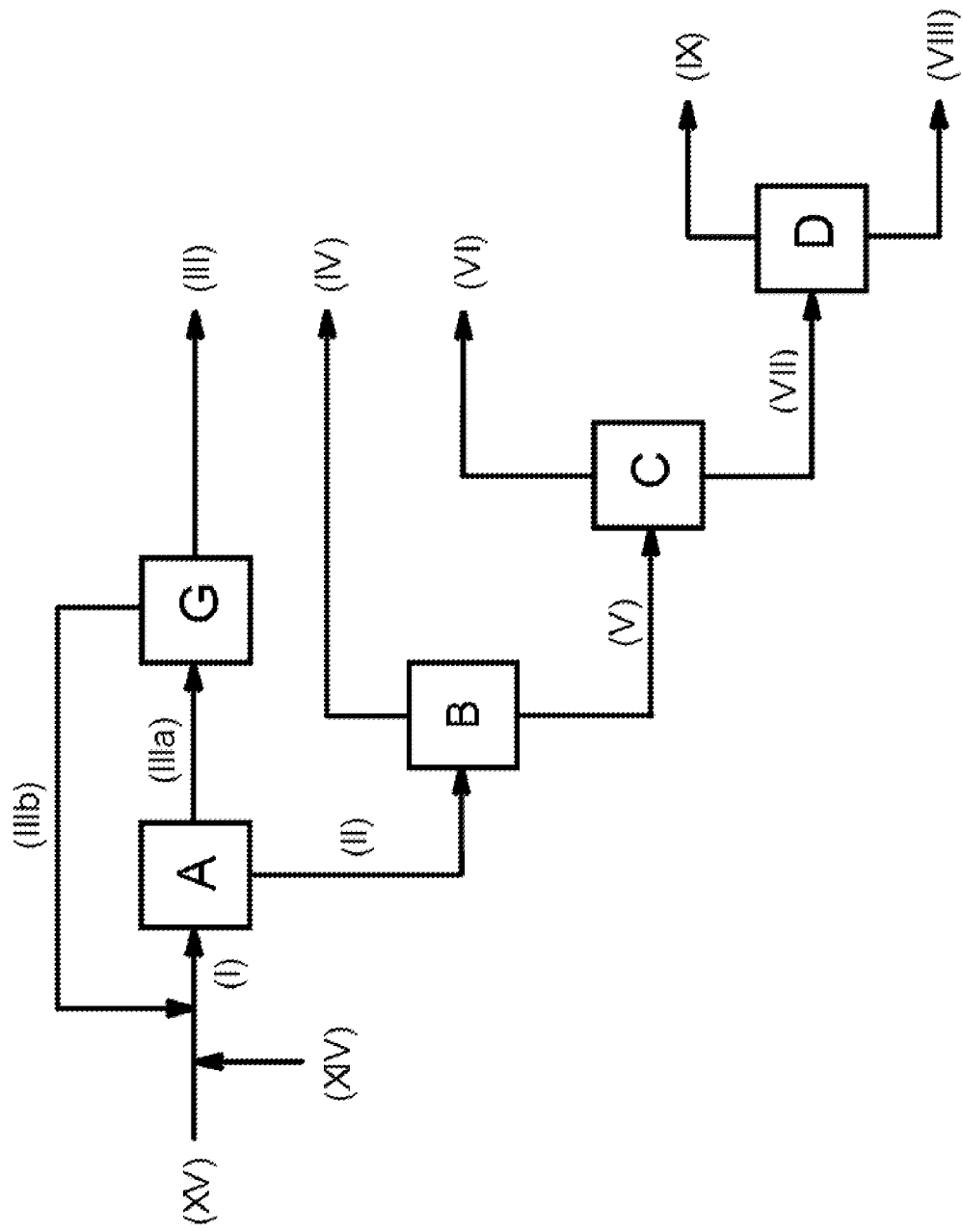

FIG. 6 shows a simplified block diagram of an interconnection for preparation of methanol according to the prior art. The labels therein have the following meanings:

(A) methanol synthesis unit
(B) expansion unit (low pressure expansion)
(C) low boiler column
(D) pure methanol column
(G) pressure swing adsorption
(I) carbon dioxide and hydrogen containing stream
(II) methanol-and water-enriched crude methanol
(IIIb) recovered hydrogen from pressure swing adsorption (G)
(III) off-gas from pressure swing adsorption (G)
(IV) expansion gas from expansion unit (B)
(M) degassed crude methanol stream
(VI) low boiler stream from low boiler column (C)
(VII) bottom stream from distillation apparatus (C)
(VIII) high boiler stream from pure methanol column (D)
(IX) pure methanol
(XIV) hydrogen feedstock ("fresh hydrogen")
(XV) carbon dioxide feedstock ("fresh carbon dioxide").

The conversion of carbon dioxide and hydrogen to methanol is effected in what is called a methanol synthesis unit (A) at a temperature of 150 to 300° C. and a pressure of 3 to 10 MPa abs in the presence of a methanol synthesis catalyst. The carbon dioxide and hydrogen containing stream (I) is a mixture containing carbon dioxide obtained by the combustion of stream (III) and at least one of the streams (IV) and (VI), carbon dioxide supplied by stream (XV) and hydrogen supplied by stream (XIV). The above mentioned feedstocks and recycle streams are described further down in connection with the relevant process stages and process variants.

In general, the streams fed to the methanol synthesis unit (A) have in total, calculated as one combined stream, a stoichiometric number S $$S = \frac{n(H_2) - n(CO_2)}{n(CO) + n(CO_2)} \tag{6}$$

in the range from 1 to 5, preferably $\geq 1.3$, more preferably $\geq 1.5$, particularly preferably $\geq 1.8$, very particularly preferably $\geq 1.9$ and most preferably $\geq 2$, and preferably $\leq 4$, more preferably $\leq 3$, particularly preferably $\leq 2.5$ and most preferably $\leq 2.3$. Since the internal cycle stream within the methanol synthesis unit (A) is not considered in the above-mentioned consideration, the stoichiometric number S of the carbon dioxide and hydrogen containing stream (I) entering the methanol synthesis reactor deviates from the above-mentioned values.

In order to enable the conversion of the carbon dioxide and hydrogen containing stream (I) at a pressure of 3 to 10 MPa abs in the methanol synthesis unit (A), the carbon dioxide and hydrogen containing stream (I) is typically compressed to the desired pressure by means of a compressor and converted in a reactor under the conditions specified.

The conversion is preferably effected at a temperature of $\geq 170°$ C. and more preferably at $\geq 190°$ C., and preferably at $\leq 280°$ C. and more preferably at $\leq 260°$ C. With regard to the pressure, the conversion is effected preferably at $\geq 4$ MPa abs, more preferably at $\geq 6$ MPa abs and preferably at $\leq 9$ MPa abs.

Reactors used may in principle be any reactors that are suitable for the exothermic conversion of carbon dioxide and hydrogen to methanol under the process conditions specified. As reactors for the synthesis of methanol from carbon dioxide and hydrogen, typically reactors for the synthesis of methanol from synthesis gas as generally known to the person skilled in the art can be used. Examples of these include the adiabatic and quasi-isothermal reactors, variobar reactors and what are called double-wall superconverters that are mentioned in Ullmann's Encyclopedia of Industrial Chemistry, "Methanol" chapter, Section 5.2.1 "Reactor Design", 2012 Wiley-VCH Verlag GmbH & Co. KGaA, Weinheim, Germany.

Methanol synthesis catalysts that may be used in the process of the invention are virtually any catalysts which are also suitable for the conversion of synthesis gas to methanol under the process conditions mentioned. Corresponding methanol synthesis catalysts are common knowledge to those skilled in the art. Examples of these include the copper- and zinc-containing heterogeneous catalysts that are mentioned in Ullmann's Encyclopedia of Industrial Chemistry, "Methanol" chapter, Section 4.2 "Catalysts", 2012 Wiley-VCH Verlag GmbH & Co. KGaA, Weinheim, Germany. In general, these also comprise further elements, for example aluminum, rare earths or chromium.

The conversion of the carbon dioxide and hydrogen containing stream (I) forms methanol and water in accordance with reaction equation (2) and some carbon monoxide and water in accordance with reaction equation (3), whereby carbon monoxide is also converted to methanol in accordance with reaction equation (1).

(2)

(3)

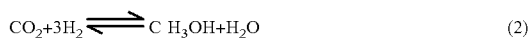
(1)

A typical by-product formed is dimethyl ether. In addition, full hydrogenation of carbon dioxide or carbon monoxide also gives rise to methane as a further by-product. The reaction mixture produced in the reactor thus comprises methanol, water, dimethyl ether, carbon monoxide, carbon dioxide, hydrogen and methane. Additionally formed under the reaction conditions mentioned, however, are typically also further by-products, for example methyl formate, acetic acid, higher alcohols having carbon numbers of ≥2, esters and ethers having carbon numbers of >2, and also paraffins.

For separation of the complex reaction mixture, a methanol- and water-enriched crude methanol stream (II) is first condensed out. For this purpose, the reaction mixture produced in the reactor is typically fed to a condenser. Condensers used may be the apparatuses known to the person skilled in the art that are suitable for obtaining a methanol- and water-enriched condensate by controlled cooling under the present conditions. In general, the reaction mixture is cooled down to a temperature below the dew point of methanol. In accordance with the solubilities and vapor pressures of the components present in the reaction mixture, the methanol- and water-enriched crude methanol stream (II) still comprises gases dissolved therein, for example hydrogen, carbon monoxide, carbon dioxide, dimethyl ether, methane, and higher-boiling components than methanol. The crude methanol stream (II) condensed out is then discharged from the methanol synthesis unit (A) for further workup and guided to stage (b).

The uncondensed gas stream especially comprises the unconverted carbon dioxide, carbon monoxide and hydrogen feedstocks, and methane. In order to obtain a high partial pressure of hydrogen and carbon dioxide as well as carbon monoxide, a portion of the uncondensed gas stream is typically discharged. This discharged gas stream can be sent to a removal of hydrogen in order to reduce the demand of the hydrogen feedstock (XIV). A high partial pressure of hydrogen in the reactor reduces the formation of secondary components and especially also suppresses the Fischer-Tropsch reaction. The predominant portion of the uncondensed gas stream is recycled into the methanol synthesis unit as cycle gas and guided over the methanol synthesis catalyst in order to achieve maximum exploitation of the carbon dioxide and hydrogen containing feedstocks and hence high yields of methanol.

Accordingly, the methanol synthesis unit (A) in stage (a) advantageously comprises a compressor for compression of the carbon dioxide and hydrogen containing stream, a reactor for conversion of the compressed carbon dioxide and hydrogen, a condenser for condensing out the crude methanol stream (II), and a conduit for recycling of uncondensed gas to the reactor.

Depending on the amount of hydrogen supplied with the carbon dioxide, it may be already possible to establish a stoichiometric number S of >2 at the reactor inlet. Preferably, in the process of the invention, by means of recycled synthesis cycle gas within the methanol synthesis unit (A) and optionally also by means of the additional recycling of hydrogen from the further workup of the discharged synthesis cycle gas, a stoichiometric number S at the reactor inlet of preferably ≥2.5 and more preferably of ≥2.8, and preferably ≤4 and more preferably of ≤3.8, is established.

The uncondensed gas stream that has not been recycled as synthesis cycle gas is discharged from the methanol synthesis unit (A) as gaseous stream (III) and guided to stage (e) of the invention. The amount of gas stream (III) to be discharged is found from the mass balance of the streams supplied to and removed from the methanol synthesis unit (A).

In stage (b) of the process of the invention, the crude methanol stream (II) that has been condensed out in stage (a) and discharged from the methanol synthesis unit (A) is expanded in an expansion unit (B) to a pressure of 0.1 to 2 MPa abs, and an expansion gas (IV) comprising carbon dioxide and methane and a degassed crude methanol stream (V) enriched with methanol and water are obtained. The expansion is typically effected in an apparatus in which gas phase and liquid phase can be efficiently separated from one another. Typically, the apparatus is a liquid separator. Suitable apparatuses for this purpose are known to those skilled in the art.

The expansion is preferably effected to a pressure of ≥0.2 MPa abs and more preferably to ≥0.4 MPa abs, and preferably to ≤1.5 MPa abs and more preferably to ≤1 MPa abs. In general, the temperature of the expanded mixture is 0 to 150° C., preferably 10° C. and more preferably ≥20° C., and preferably ≤120° C. and more preferably ≤60° C.

The degassed crude methanol stream (V) has been further enriched in methanol and water, but also comprises further components in accordance with the solubilities and vapor pressures of the components present in the crude methanol stream (II), for example gases dissolved therein such as hydrogen, carbon dioxide, carbon monoxide, dimethyl ether, methane or higher-boiling components than methanol.

The expansion gas (IV) comprising carbon dioxide, methane and typically also hydrogen and carbon monoxide is preferably guided to stage (e) of the invention. Alternatively, the expansion gas (IV) can, however, also be discharged from the methanol synthesis plant and, for example, be utilized thermally or disposed of in some other way. However, preference is given to the utilization thereof within the methanol synthesis plant as feed stream to the combustion unit (E).

In stage (c) of the process of the invention, the degassed crude methanol stream (V) obtained in stage (b) is separated by distillation in a distillation apparatus (C) into a low boiler stream (VI) comprising carbon dioxide and dimethyl ether, and a bottom stream (VII) enriched with methanol and water. Useful distillation apparatuses in principle include the apparatuses known to the person skilled in the art for such separation tasks or those to be designed by applying common knowledge in the art. Typically, the distillative separation in step (c) is effected in a single distillation column, although it is of course also possible to operate multiple distillation columns in parallel. As well as the actual column body with internals, the distillation column, as usual, also comprises a top condenser and a reboiler. The column body may have been equipped, for example, with structured packings, random packings or trays. The distillation apparatus (C) may be designed and operated by the common knowledge of the person skilled in the art.

The low boiler stream (VI) separated off by distillation comprises primarily carbon dioxide and dimethyl ether as low boilers that have been separated off and, based on the composition of the degassed crude methanol stream (V), further low boilers, for example methane, and also, depending on the separation performance and mode of operation of the distillation apparatus, methanol or higher-boiling components than methanol, for example water. The low boiler stream (VI) comprising carbon dioxide and dimethyl ether is likewise preferably guided to stage (e) of the invention. If the expansion gas (IV) is sent to the combustion unit (E) and hence reused directly within the methanol synthesis plant, the low boiler stream (VI) can alternatively also be discharged from the methanol synthesis plant and, for example, utilized thermally or disposed of in some other way. However, preference is given to utilization thereof within the methanol synthesis plant as feed stream to the combustion unit (E).

The methanol- and water-enriched bottom stream (VII) additionally also comprises further components that are higher-boiling than methanol, for example higher-boiling by-products than methanol from the methanol synthesis, for instance acetic acid, higher alcohols, higher esters, higher ethers or paraffins.

To obtain the methanol, finally, in stage (d), a water-containing high boiler stream (VIII) is separated from the bottom stream (VII) obtained in stage (c) in a further distillation apparatus (D) and methanol is obtained by distillation as stream (IX). Useful distillation apparatuses for stage (d) in principle include the apparatuses known to the person skilled in the art for such separation tasks or those to be designed by applying common knowledge in the art. In principle, the distillative separation in stage (d) can be effected in a single distillation column. As well as the actual column body with internals, the distillation column, as usual, also comprises a top condenser and a reboiler. The column body may have been equipped, for example, with structured packings, random packings or trays. It is of course also possible to operate multiple distillation columns in parallel or to remove the methanol stepwise in multiple distillation columns. The distillation apparatus (D) may be designed and operated by the common knowledge of the person skilled in the art.

Methanol is typically obtained as top product as stream (IX). But it is also possible in principle to obtain methanol as what is called a side stream and to remove low boilers still present as a top stream.

A variant which is attractive in terms of energy is called the two-pressure distillation. In this variant, two distillation columns are connected in series and coupled to one another in terms of energy. The first distillation column is operated under pressure, typically at 0.5 to 1.5 MPa abs, and methanol is removed overhead as low boiler. The first distillation column is operated in such a way that some of the methanol remains in the bottoms, and these are sent to a second distillation column. The second distillation column is operated at a lower pressure, for example atmospheric pressure. The bottom of the second distillation column is coupled in terms of energy to the low boiler stream from the first distillation column, meaning that the amount of heat released on cooling of the low boiler stream from the first distillation column serves to heat up the second distillation column. In the second distillation column too, methanol is removed overhead as low boiler. The high boilers obtained in the bottom of the second distillation column are removed and discharged. The construction and operation of the two-pressure distillation and especially of the two-pressure distillation for obtaining methanol are known to the person skilled in the art.

The high boiler stream (VIII) comprises water and also further components that are higher-boiling than methanol, for example higher-boiling by-products than methanol from the methanol synthesis, for instance acetic acid, higher alcohols, higher esters, higher ethers or paraffins. This stream can be sent to a wastewater treatment, for example.

Via stream (IX), methanol can be obtained in a high purity of ≥95% by weight, preferably ≥98% by weight and more preferably ≥99% by weight. Accompanying substances include residual amounts of low and high boilers that have not been removed completely by distillation, especially water, and very small amounts of ethanol, esters and ethers.

In the stepwise workup of the reaction mixture to obtain the methanol as stream (IX), streams (III), (IV) and (VI) are separated off. However, these still contain components of value, for example carbon dioxide, carbon monoxide, methane and dimethyl ether. The core of the invention is besides the use of hydrogen and carbon dioxide as feedstocks, the substantial physical reuse of the carbon in these components of value mentioned in the preceding sentence for further synthesis of methanol with simultaneous avoidance of carbon dioxide emission.

The stages (e) to (g) that are essential to the invention are elucidated in detail hereinafter.

The process of the invention comprises
e) feeding the carbon dioxide, carbon monoxide, dimethyl ether and methane components of value in stream (III) and in at least one of the two streams (IV) and (VI) to a combustion unit (E) and combusting them therein with supply of an oxygenous gas (X) having an oxygen content of 30% to 100 vol.-%, forming a carbon dioxide-containing flue gas (XI),
f) separating a carbon dioxide-enriched stream (XIII) from the carbon dioxide-containing flue gas (XI) from stage (e) in a carbon dioxide recovery unit (F) to form an off-gas stream (XII), and
g) recycling the carbon dioxide-enriched stream (XIII) separated off in the carbon dioxide recovery unit (F) from stage (f) to the methanol synthesis unit (A) of stage (a) as a carbon dioxide containing source of stream (I).

Preferably, in stage (e), the carbon dioxide, carbon monoxide, dimethyl ether and methane components of value in streams (III), (IV) and (V) are fed to the combustion unit (E).

Since the methane and dimethyl ether components of value in streams (III), (IV) and (VI), but also other carbon-containing by-products present therein, cannot be used directly in this form as reactants for the methanol synthesis, it is necessary first to convert them chemically to a suitable form. The solution of the invention therefore envisages combusting these in a combustion unit (E) to form a carbon dioxide-containing flue gas. The conversion to carbon dioxide makes it possible also to reuse the components of value methane, dimethyl ether and further carbon-containing by-products as reactant in the methanol synthesis. Therefore, in the process of the invention, streams (III) and in at least one of the two streams (IV) and (VI), and preferably all three streams (III), (IV) and (VI) are first sent to a combustion unit (E). The combustible components of value are burned therein with supply of an oxygenous gas (X) having an oxygen content of 30% to 100 vol.-%. The combustion is typically effected in what is called a combustion chamber with formation of carbon dioxide and water. The combustion is typically effected at atmospheric pressure. But it is also possible to conduct the combustion at a lower or higher pressure. For the sake of completeness, a pressure range from 0.05 to 0.5 MPa abs is stated.

Combustion chambers used may in principle be any apparatuses suitable for the highly exothermic oxidation of a corresponding stream comprising carbon monoxide, methane and dimethyl ether with an oxygenous gas having an appropriate oxygen content. Suitable combustion chambers are known to the person skilled in the art or can be designed and operated with the common knowledge of the person skilled in the art. Examples include, for instance, adiabatic combustion chambers or reactors with outcoupling of heat, such as directly fired steam generators, for instance in the form of water-tube boilers or flame-tube or smoke-tube boilers.

A significant advantage of the inventive use of an oxygenous gas (X) having an oxygen content of 30% to 100 vol.-% is a much higher content of carbon dioxide in the combustion gas obtained compared to the use of air with only about 21 vol.-% of oxygen. Correspondingly, in the process of the invention, compared to air as oxidizer, the proportion of unwanted inert gases, for instance nitrogen or argon, is of course also much lower.

Preferably, the combustion unit (E) is supplied with an oxygenous gas (X) having an oxygen content of ≥50 vol.-%, more preferably of ≥80 vol.-%, even more preferably of ≥90 vol.-%, in particular of ≥95 vol.-%, and especially pure oxygen. When pure oxygen is used in the combustion, this is also called an oxyfuel process.

Typically ≥90%, preferably ≥95%, more preferably ≥98% and most preferably ≥99% of the carbon in the combustible components is thus converted to carbon dioxide.

A further advantage resulting from the use of an oxygen-rich gas as oxidizer rather than air is also the distinct reduction in thermally formed nitrogen oxides $NO_x$. In the case of use of pure oxygen and only a very small content of nitrogen via the streams (III), (IV) and (VI) supplied, the formation of nitrogen oxides $NO_x$ can even be virtually completely avoided.

Furthermore, combustion processes with oxygen-rich gases as oxidizer are more energy-efficient compared to air owing to the higher combustion temperatures. For example, in the combustion of pure methane, when air is used, a theoretical combustion temperature of about 1800 to 2000° C. is found, whereas the combustion of pure methane with pure oxygen results in a theoretical combustion temperature of about 4000 to 5000° C. In order to counteract a particularly high combustion temperature, for material-related reasons in particular, in the combustion of the invention, a portion of the flue gas is typically recycled into the combustion chamber for temperature control after cooling.

Since, when an oxygenous gas (X) with a correspondingly high oxygen content is used, the flue gas formed has only a correspondingly small content of nitrogen, or is virtually free of nitrogen, a correspondingly small separation stage is generally also sufficient for separation of the nitrogen from the carbon dioxide.

In order to further increase the content of carbon dioxide in the combustion gas obtained, it is generally advantageous to reduce the water content prior to the discharge from the combustion unit (E). Typically, this is effected by simple condensing-out in a condenser. Condensers used may be the apparatuses known to the person skilled in the art that are suitable for separating water as condensate from a carbon dioxide- and water-containing gas stream by controlled cooling under the present conditions. In general, the combustion gas is cooled down to a temperature below the dew point of water. If water is condensed out, this is discharged from the combustion unit (E) as stream (XVI), and the remaining water-depleted combustion gas as carbon dioxide-containing flue gas (XI). Preferably 50% to 100%, more preferably ≥80% and most preferably ≥90% of the water present in the combustion gas is condensed out.

Figure 2:
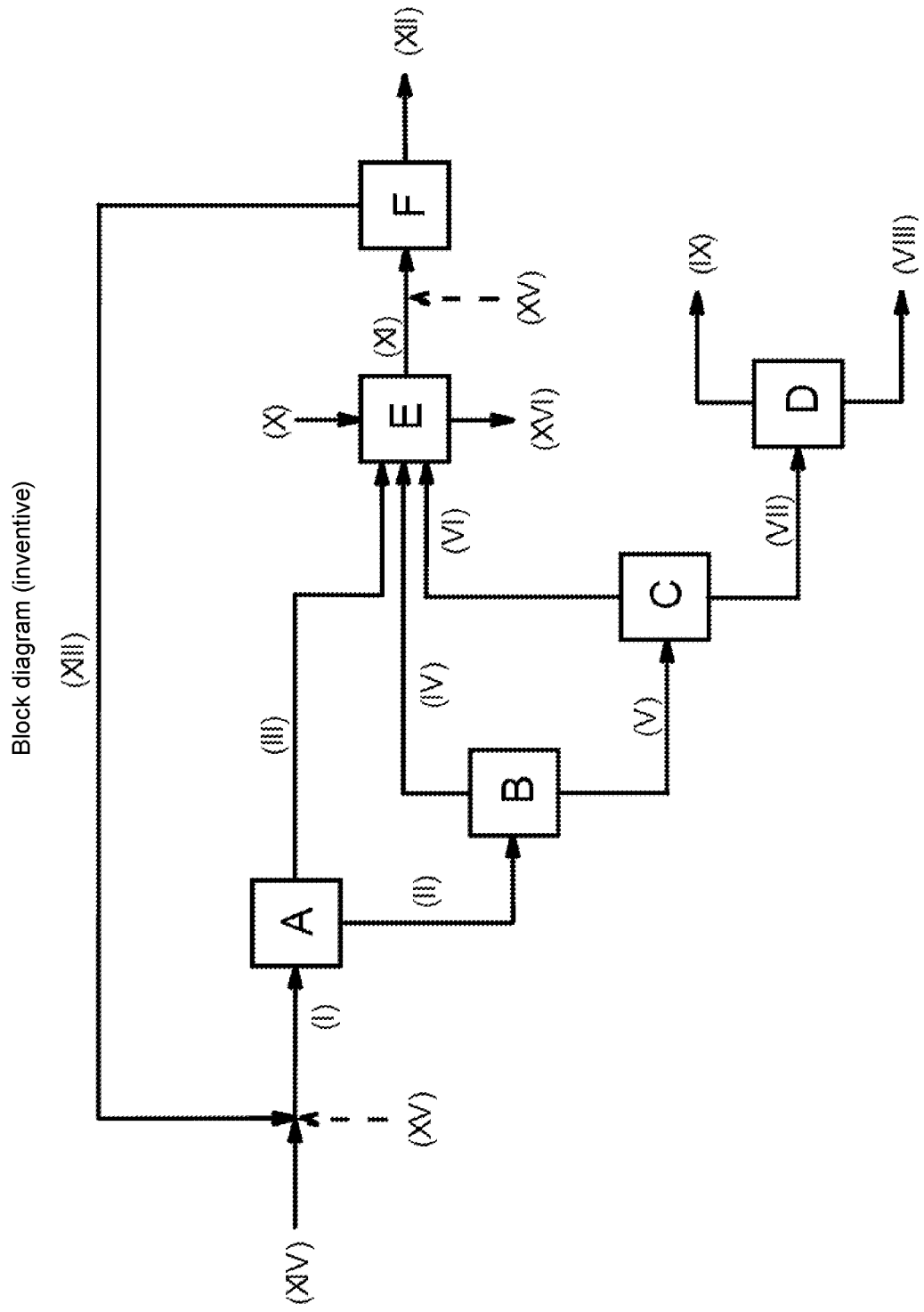
FIG. 2 shows a block diagram of a general embodiment in which water is condensed out of the combustion gas and conducted away as stream (XVI).

Preference is thus given to a process in which the combustion unit (E) in stage (e) comprises a combustion chamber and a condenser, water is condensed out of the combustion gas obtained in the combustion chamber in the condenser and conducted out of the combustion unit (E) as stream (XVI), and the remaining gaseous stream constitutes the carbon dioxide-containing flue gas (XI). FIG. 2 shows a block diagram of a general embodiment in which water is condensed out of the combustion gas and conducted away as stream (XVI).

However, it is also possible, albeit not preferable, to leave the water entirely in the combustion gas and to discharge it from the combustion unit (E) together with the carbon dioxide as carbon dioxide-containing flue gas (XI).

An appraisal illustrates the significant increase in the carbon dioxide content in the flue gas (XI) by the use of pure oxygen compared to air as oxidizer, and by the subsequent removal of the water. For instance, in a theoretical appraisal of the combustion of pure methane to give carbon dioxide and water, in the case of air as oxidizer, a carbon dioxide content in the combustion gas of around 9 vol.-%, and even after complete removal of the water, of only 12 vol.-% is achieved.

By contrast, the use of pure oxygen as oxidizer already leads to a carbon dioxide content in the combustion gas of around 33 vol.-%. By completely condensing out the water, it is even possible to achieve a theoretical carbon dioxide content of 100 vol.-%. This corresponds to an increase in the carbon dioxide content with use of pure oxygen as opposed to air by a factor of 3.7 (9 vol.-% vs. 33 vol.-%) without removal of the water, and even by a factor of 8.3 (12 vol.-% vs. 100 vol.-%) with removal of the water. Depending on the actual composition of the gas supplied to the combustion unit (E), somewhat different factors are of course found. Nevertheless, the use of pure oxygen as oxidizer leads in each case to a significantly higher carbon dioxide content in the combustion gas and, especially after the condensing-out of water, in the discharged flue gas (XI) as well.

Particularly as a result of the use of pure oxygen as oxidizer, the flue gas (XI) has a distinctly higher content of the carbon dioxide component of value. In other words, the use of pure oxygen, given the same absolute amount of carbon dioxide, results in formation of significantly less flue gas. Thus, in the process of the invention, the size of the combustion unit (E) and especially of the combustion chamber and the condenser and downstream apparatuses and conduits may have correspondingly smaller dimensions.

As well as carbon dioxide as component of value, the flue gas (XI) obtained generally still comprises various inert gases that have been fed to the combustion unit (E) via streams (III), (IV) and (VI) and/or the oxygenous gas (X), such as nitrogen or argon. Since the combustion is typically incomplete with regard to the oxygen supplied as well, the flue gas (XI) generally also comprises unconverted oxygen, typically in the range from 2% to 20 vol.-%. According to whether and to what extent water has been condensed out of the combustion gas, the flue gas (XI) also still comprises the water formed in the combustion and the fraction uncondensed after condensing out the water. In general, the flue gas (XI) discharged from the combustion unit (E) has a carbon dioxide content of 25% to 90 vol.-%, preferably ≥50 vol.-%, more preferably ≥60 vol.-% and most preferably ≥70 vol.-%, and preferably ≤85 vol.-% and more preferably ≤80 vol.-%.

For the sake of completeness, it is mentioned that in addition to stream (III) and to at least one of the streams (IV) and (VI), also further streams containing combustible carbon-containing streams may be supplied to the combustion unit (E). Such combustible carbon-containing streams can, for example, be carbon-containing by-product streams of chemical plants which are intended to be incinerated and which contain the carbon-containing compounds not highly diluted. Preferably, their carbon content is ≥50 wt.-% and more preferably ≥75 wt.-% based on the total stream of the carbon-containing compounds.

A carbon dioxide-enriched stream (XIII) is then separated in stage (f) from the carbon dioxide-containing flue gas (XI) formed in stage (e) in a carbon dioxide recovery unit (F) to form an off-gas stream (XII). The carbon dioxide recovery unit (F) used may in principle be a unit with apparatuses and processes suitable for the separation and concentration of carbon dioxide from carbon dioxide-containing gas streams that comprise, as well as carbon dioxide, also inert gases, for instance nitrogen and argon, and possibly water as further components. Corresponding apparatuses and processes are known to those skilled in the art. A general overview of possible apparatuses and processes can be found, for example, in Ullmann's Encyclopedia of Industrial Chemistry, "Carbon Dioxide" chapter, Section 13.3 "CCS-related Separation Technologies", 2014 Wiley-VCH Verlag GmbH & Co. KGaA, Weinheim, Germany. Examples include what are called the gas scrubbing processes in which the carbon dioxide is physically or chemically absorbed in what is called a gas scrubbing solvent and subsequently desorbed again, and membrane processes in which the carbon dioxide is separated off by means of a carbon dioxide-sensitive membrane.

In the case of physical absorption, the carbon dioxide is absorbed in an absorber under elevated pressure in a suitable solvent, for instance methanol, N-methylpyrrolidone or polyethylene glycol dimethyl ether, and subsequently desorbed again under expansion in a desorber. The carbon dioxide-depleted solvent is typically recycled back to the absorber. The physical absorption typically requires pressures in the range from about 2 to 5 MPa abs. However, since the carbon dioxide-containing flue gas (XI) is typically only at a pressure of 0.1 to 0.3 MPa abs, it would first have to be compressed with expenditure of energy.

In the process of the invention, preference is therefore given to chemical absorption in a solvent that chemically binds carbon dioxide. Chemical absorption generally does not require higher pressures, and so there is no need first to compress the carbon dioxide-containing flue gas (XI) in an energy-intensive manner. Chemically active solvents that are mentioned are basic solvents in particular. In chemical absorption, in the carbon dioxide recovery unit (F) in stage (f), carbon dioxide is absorbed from the carbon dioxide-containing flue gas (XI) in an absorber in a basic solvent to form the off-gas stream (XII) and subsequently desorbed again at higher temperature in a desorber. The carbon dioxide-depleted solvent is typically recycled back to the absorber.

Preference is therefore given to a process in which, in the carbon dioxide recovery unit (F) in stage (f), carbon dioxide is absorbed from the carbon dioxide-containing flue gas (XI) in an absorber in a basic solvent to form the off-gas stream (XII), a carbon dioxide-enriched stream (XIII) is released from the carbon dioxide-laden solvent in a desorber, and the carbon dioxide-depleted solvent is returned to the absorber.

The basic solvents are typically aqueous solutions of basic inorganic or organic substances. Basic inorganic substances include, for instance, salts of hydrogencarbonate, and basic organic substances include organic amines. Typically, the water content of the aqueous solutions is 20% to 80% by weight, preferably 40% by weight and more preferably 50% by weight.

The basic solvent used in the process of the invention is more preferably an aqueous solution of an organic amine. The amines may be linear or cyclic, unbranched or branched compounds. Suitable amines are mentioned, for example, in US 2008/236,390, US 2010/192,770 or US 2011/094,381. The organic amines preferably have a molar mass of 50 to 500 g/mol. Particular preference is given to the use of monoethanolamine, piperazine, 2-amino-2-methyl-1-propanol, triethylenediamine, N-methyldiethanolamine, tert-butylaminoethoxyethanol, very particular preference to that of N-methyldiethanolamine.

Typically, in the chemical absorption, the carbon dioxide-containing flue gas (XI) is contacted with the basic solvent in the absorber at a temperature of 10 to 100° C., preferably ≥20° C., and preferably ≤60° C. and more preferably ≤40° C. Absorbers used may in principle be any apparatuses suitable for absorption of carbon dioxide from a carbon dioxide-containing flue gas stream. Suitable apparatuses for the purpose are known to the person skilled in the art and can be designed with common knowledge in the art. Typically, absorption is accomplished using what are called absorption columns. For better heat and mass transfer, these advantageously comprise structured packings or trays. On contact with the basic solvent, the carbon dioxide is chemically bound therein. The components not absorbed in the basic solvent are conducted out of the absorption column as off-gas stream (XII) as what is called the purge stream. The carbon dioxide-laden solvent is drawn off at the bottom of the absorber, fed to the absorber and stripped with steam therein in order to release the carbon dioxide again. Advantageously, the desorber is preferably operated at a temperature of 40 to 110° C. higher than the absorber. Suitable apparatuses for the purpose are likewise known to the person skilled in the art and can be designed with common knowledge in the art. Typically, desorption is accomplished using what are called desorption columns. For better heat and mass transfer, these also advantageously comprise structured packings or trays. Water is first advantageously condensed out of the desorption stream obtained at the top of the desorber. The water condensed out can then, for example, be recycled back into the carbon dioxide recovery process. The solvent that has been depleted of carbon dioxide and water is then recycled to the absorber.

Both absorber and desorber are typically operated at 0.1 to 0.3 MPa abs; the exact pressures are generally guided by the downstream process steps and can be determined easily by the person skilled in the art. Alternatively, the absorption can also be operated at higher pressures. The carbon dioxide absorption capacity of the solvent in that case is higher than under conditions close to ambient pressure. As a result, the regeneration in the desorber is also more energy-efficient. However, in this variant, the carbon dioxide-containing flue gas (XI) would have to be compressed, which has an adverse effect on the overall energy balance. Therefore, absorber and desorber are preferably operated at 0.1 to 0.3 MPa abs.

Since the desorption is typically effected at higher temperature than the absorption, the carbon dioxide-laden solvent withdrawn from the absorber should be heated, and the carbon dioxide- and water-depleted solvent withdrawn from the desorber should be cooled for reuse thereof in the absorber. It is therefore particularly advantageous for the energy efficiency of the carbon dioxide recovery to use what is called a crossflow heat exchanger, in which the warmer solvent from the desorber heats up the colder solvent from the absorber. The use of further solvent heat exchangers can further increase the energy efficiency of the process. The exact setting of the temperature of the carbon dioxide-depleted solvent for use thereof in the absorber can then be effected, for example, by means of an air or water cooler.

In addition, it is possible to further increase the energy efficiency of the carbon dioxide recovery by further thermal integration measures, for example by the use of a liquid cooler in the lower absorber region. Solvent losses can also be reduced by further measures. For example, it is possible, and advantageous in the case of solvents having a non-negligible vapor pressure, to guide the gas stream through a scrubbing bed in the upper absorber region and to cool the liquid phase via direct cooling with a circulation cooler.

In order to compensate for losses of solvent, which generally cannot be entirely avoided in spite of various countermeasures, solvent or individual solvent components are typically supplied as what is called a makeup stream. It is thus possible to keep the levels in the two columns constant over time. Typically, the supply is effected at the top of the absorber.

The carbon dioxide recovery unit (F) selectively removes the carbon dioxide from the flue gas (XI) and recovers it in the form of a carbon dioxide-enriched stream (XIII) for further use in the methanol synthesis. Typically, the carbon dioxide-enriched stream (XIII) comprises carbon dioxide at a level of 80% to 100 vol.-% on an anhydrous basis, preferably ≥97 vol.-% on anhydrous basis, and small amounts of extraneous gases, for example nitrogen, oxygen or argon, but these are typically below 0.3 vol.-% on an anhydrous basis. In addition, the carbon dioxide-enriched stream (XIII) typically also comprises water, which, however, has already been excluded in the abovementioned percentages by volume.

The carbon dioxide recovery processes mentioned are notable for a relatively high carbon dioxide recovery rate, the carbon dioxide recovery rate being understood to mean the ratio between the amount of carbon dioxide which is fed to the carbon dioxide recovery unit (F) via the carbon dioxide-containing flue gas (XI) and the amount of carbon dioxide which is conducted out of the carbon dioxide recovery unit (F) via the carbon dioxide-enriched stream (XIII). The processes mentioned can easily achieve carbon dioxide recovery rates of 90% to almost 100%. The carbon dioxide recovery rate is preferably ≥95%, more preferably ≥98% and most preferably ≥99%, and preferably ≤99.9%.

The off-gas stream (XII) comprises the components of the flue gas (XI) that have not been separated off via the carbon dioxide-enriched stream (XIII), especially inert gases, for instance nitrogen or argon, but also oxygen and water that has not been separated off in the carbon dioxide recovery unit (F). By means of the off-gas stream (XII), in particular, inert gases are thus selectively discharged from the methanol synthesis process and hence unwanted accumulation is counteracted. The off-gas stream (XII) thus functions not just as off-gas stream for the carbon dioxide recovery unit (F) but at the same time also assumes the important function of what is called the purge stream for discharge of inert gases from the methanol synthesis.

The carbon dioxide-enriched stream (XIII) separated off in the carbon dioxide recovery unit (F) is subsequently recycled to the methanol synthesis unit (A) of stage (a) as a carbon dioxide containing source of stream (I).

Since the carbon dioxide-enriched stream (XIII) generally still comprises small amounts of oxygen, typically in the order of magnitude of a few ppm by volume to a few hundred ppm by volume, and oxygen has an adverse effect on the methanol synthesis with regard to catalyst service life and performance, it is advantageous to reduce the oxygen content of stream (XIII). In principle, it is possible for this purpose to use various processes capable of removing small amounts of oxygen from a carbon dioxide-containing stream. A simple process for this purpose is the catalytic hydrogenation of the oxygen to water. Examples of suitable catalysts for this purpose include copper- or precious metal-containing fixed bed catalysts. Suitable processes and the design and operation thereof are known to those skilled in the art. It is thus advantageous to catalytically hydrogenate stream (XIII) prior to recycling thereof to the methanol synthesis unit (A) to deplete the oxygen. By the hydrogenation mentioned, it is easily possible to reduce the oxygen content to values <1 ppm by volume.

Besides stages (e) to (g), which enable a virtually complete physical utilization of the carbon-containing components of value for methanol synthesis and with avoidance of emission of carbon dioxide, it is also essential to the invention to use hydrogen and carbon dioxide as raw materials. These raw materials allow the use of a variety of environmentally friendly sources. The respective feedstocks can be supplied to the methanol synthesis plant at different suitable input points.

The hydrogen feedstock is supplied to the methanol synthesis unit (A) of stage (a) as a hydrogen containing source of stream (I). It is generally irrelevant whether the hydrogen feedstock (XIV) is supplied to the carbon dioxide-enriched stream (XIII) or directly to the cycle gas inside the methanol synthesis unit (A) However, it is important that the hydrogen feedstock is thoroughly mixed with the other streams before entering the methanol synthesis reactor. Therefore, the hydrogen feedstock (XIV) is preferably supplied somewhere upstream before the compressor of the methanol synthesis reactor, whereby somewhere upstream can be directly before as well as in a long distance before, such as an addition to the carbon dioxide-enriched stream (XIII) shortly after stream (XIII) is released from the carbon dioxide recovery unit (F).

In order to avoid the accumulation of substances extraneous to the reaction and especially of inert gases in the methanol synthesis, it is desirable to supply hydrogen of maximum purity or at least hydrogen having only a low content of substances extraneous to the reaction. The supplied hydrogen feedstock (XIV) preferably has a hydrogen content of ≥80 vol.-%, more preferably of ≥90 vol.-%, even more preferably of ≥95 vol.-%, especially of ≥99 vol.-% and in particular of ≥99.5 vol.-%.

The hydrogen feedstock (XIV) may in principle come from a wide variety of different sources. Examples include the supply of hydrogen from other production plants in which hydrogen is formed deliberately or as a by-product, for example from steamcrackers or refineries, from the processing of synthesis gas, from the cracking of hydrocarbons, for example the pyrolysis of methane and/or higher hydrocarbons, or from the electrolysis of water. Further examples of production plants in which hydrogen is formed include the conversion of butane-1,4-diol to γ-butyrolactone, the dehydrogenation of propane to propene, the dehydrogenation of methanol to formaldehyde, the dehydrogenation of cyclohexanol to cyclohexanone, the dehydrogenation of cyclododecanol to cyclododecanone, and the electrochemical production of chlorine or other halides.

Particular preference is given to the use of hydrogen from renewable sources in which the hydrogen is produced without or with only a minimum of carbon dioxide emission. In this connection, particular mention should be made of the electrolysis of water by solar, wind or water energy.

The amount of hydrogen to be fed in with stream (XIV) is generally guided by the desired stoichiometric number S at the reactor inlet.

The carbon dioxide feedstock is supplied as stream (XV) to the carbon dioxide-containing flue gas (XI) and/or to the methanol synthesis unit (A) of stage (a) as a carbon dioxide containing source of stream (I). These options for the carbon dioxide addition mainly differ by the fact that stream (XI) is a flue gas stream containing diluted carbon dioxide and some secondary components such as residual oxygen or as the case may be also nitrogen or water, whereas stream (XIII) and other streams fed to the methanol synthesis unit (A) already contain the educts carbon dioxide and hydrogen in an enriched form. As a consequence, the flue gas stream (XI) tolerates the addition of diluted carbon dioxide but also of concentrated carbon dioxide, whereas it would be detrimental to supply diluted carbon dioxide to the methanol synthesis unit (A). These aspects enable the use of a broad variety of carbon dioxide feedstocks (XV) with very low carbon dioxide contents as well as with very high carbon dioxide contents. Carbon dioxide feedstocks (XV) containing diluted carbon dioxide are preferably supplied to the carbon dioxide-containing flue gas (XI), whereas carbon dioxide feedstocks (XV) containing carbon dioxide in a high concentration are preferably supplied to the methanol synthesis unit (A).

It is therefore preferred to supply a carbon dioxide feedstock (XV) containing 5 to 95 vol.-% carbon dioxide based on the gaseous feedstock to the carbon dioxide-containing flue gas (X). Typical carbon dioxide feedstock with such a carbon dioxide content are flue gases from a variety of different sources as elucidated in more detail below. Since flue gases based on technical processes using air as oxidation medium typically contain 5 to 15 vol.-% carbon dioxide, the carbon dioxide feedstock (XV) supplied to the carbon dioxide-containing flue gas (X) contains more preferably 5 to 15 vol.-% carbon dioxide. Typical by-products are, for example, nitrogen, oxygen, argon or water. In view of a proper operation of the carbon dioxide removal unit (F) and particularly if unit (F) is a chemical absorption unit, it is expedient to supply a carbon dioxide feedstock (XV) having ≤2 vol.-ppm of $SO_x$, ≤200 vol.-ppm of $NO_x$, ≤1 vol.-ppm of HCl, ≤1 vol.-ppm of acids and ≤1 vol.-ppm of $H_2$. It is generally irrelevant whether the carbon dioxide feedstock (XV) which is supplied to the carbon dioxide-containing flue gas (XI) is supplied to nearby the combustion unit (E), nearby the carbon dioxide recovery unit (F), or somewhere in between.

Moreover, it is preferred to supply a carbon dioxide feedstock (XV) containing 95 to 100 vol.-% carbon dioxide based on the gaseous feedstock to the methanol synthesis unit (A). Typical carbon dioxide feedstock with such a carbon dioxide content are, for example, feedstocks from diverse sources which are already concentrated in its carbon dioxide content, or from processes in which already streams with such a high carbon dioxide content are obtained. It is generally irrelevant whether the carbon dioxide feedstock (XV) is supplied to the carbon dioxide-enriched stream (XIII) or directly to the cycle gas inside the methanol synthesis unit (A). However, it is important that the carbon dioxide feedstock (XV) is thoroughly mixed with the other streams before entering the methanol synthesis reactor. Therefore, the carbon dioxide feedstock (XV) is preferably supplied somewhere upstream before the compressor of the methanol synthesis reactor. This, of course, includes the supply of the carbon dioxide feedstock (XV) to the carbon dioxide-enriched stream (XIII) shortly after stream (XIII) is released from the carbon dioxide recovery unit (F).

For the sake of completeness, it is explicitly mentioned that the carbon dioxide can also be supplied simultaneously to the carbon dioxide-containing flue gas (XI) and to the methanol synthesis unit (A). This is for instance advantageous if a diluted as well as a concentrated carbon dioxide stream is available. It shows the high flexibility of the process of the invention.

Irrespective of whether the carbon dioxide feedstock (XV) is supplied to the carbon dioxide-containing flue gas (XI) or to the methanol synthesis unit (A) of stage (a), it should preferably be free or substantially free of metals, phosphorus, and half-metals like silica, germanium, arsenic, selenium, antimony, tellurium and their compounds, which would be noticeably detrimental to the methanol preparation process or the methanol purity. Regarding the carbon dioxide feedstock (XV) supplied to the methanol synthesis unit (A), it should preferably also be free or substantially free of halogen and sulfur compounds.

The carbon dioxide feedstock (XV) may in principle come from a wide variety of different sources. Examples include the supply of carbon dioxide from power plants based on fossil fuels such as coal or natural gas, renewable sources such as based on biomass, plastics such as not recyclable plastic waste, and carbon containing residual materials from chemical plants in which carbon containing fuels are used for generating heat, or from waste incineration plants. Further examples include the supply of carbon dioxide from metallurgical plants such as blast furnaces or steal production, from cement plants, whereby the carbon dioxide may not only derive from the heating process but also from the calcination of the calcium carbonate to form calcium oxide, or from chemical production complexes in which carbon dioxide is produced as a by-product such as the production of ethylene oxide from ethylene and oxygen, the production of ammonia from natural gas, coal or oil based hydrocarbons, the production of synthesis gas based on natural gas, gasification of coal or oil based hydrocarbons, renewable feedstocks, plastics like not recyclable plastic waste, or other carbon containing residual materials. Besides the above described sources, the carbon dioxide may also come from the processing of ambient air from which carbon dioxide may be extracted. The initially obtained carbon containing stream may be first purified, if required, and/or the carbon dioxide concentrated to form the desired carbon dioxide feedstock (XV).

In case of carbon dioxide based on renewable sources or air, the carbon cycle is a closed circuit.

For the sake of completeness, it is mentioned that besides the process of the invention, streams (III), (IV) and/or (VI) may, instead of feeding them to the combustion unit (E) and the flue gas obtained therein to the carbon dioxide recovery unit (F), be fed to an external combustion or incineration unit. Such an external combustion or incineration unit may be fueled with a carbon-containing fuel which is, for example, burned with air. As examples of carbon-containing fuel coal or natural gas, renewable sources, plastics and carbon containing residual materials from chemical plants are mentioned. The flue gas may then be fed to an external carbon dioxide recovery unit in order to recover the carbon dioxide, which could then be used as a carbon dioxide feedstock (XV).

The process of the invention enables besides the supply of hydrogen and carbon dioxide as raw materials also the supply of a carbon monoxide containing feedstock such as carbon monoxide as such as well as synthesis gas. However, it is preferred to supply carbon dioxide in an amount that 50 to 100% of the carbon bound in the methanol (IX) is based on carbon dioxide supplied by the carbon dioxide feedstock (XV). More preferably, the fraction of carbon bound in the methanol (IX) which is based on carbon dioxide supplied by the carbon dioxide feedstock (XV) is ≥75%, particularly preferably ≥90%, very particularly preferably ≥95% and most preferably ≥98%.

The hydrogen feedstock (XIV) and the carbon dioxide feedstock (XV) are preferably supplied to the methanol production complex of the invention in an amount adjusted to the stoichiometry of the whole methanol process, including the formation of the small amount of by-products which are removed. Due to this, the practical molar ratio of hydrogen to carbon dioxide supplied by the above-mentioned streams (XIV) and (XV) is slightly above 3 and typically in the range of 3.0 to 3.2, and preferably in the range of 3.0 to 3.1. Accordingly, it is also advantageous to adjust the supply of the hydrogen feedstock (XIV) and the carbon dioxide feedstock (XV) to the stoichiometry of the whole methanol process if besides these streams also an additional carbon monoxide source such as synthesis gas is supplied.

The process of the invention for preparing methanol is conducted continuously.

It is thus possible by the process steps of the invention to reuse the carbon in the components of value specifically for the further synthesis of methanol, i.e. to produce further product of value, and at the same time to avoid emission of carbon dioxide from the methanol synthesis.

The methanol synthesis can thus be operated free of carbon dioxide emissions.

Figure 3:
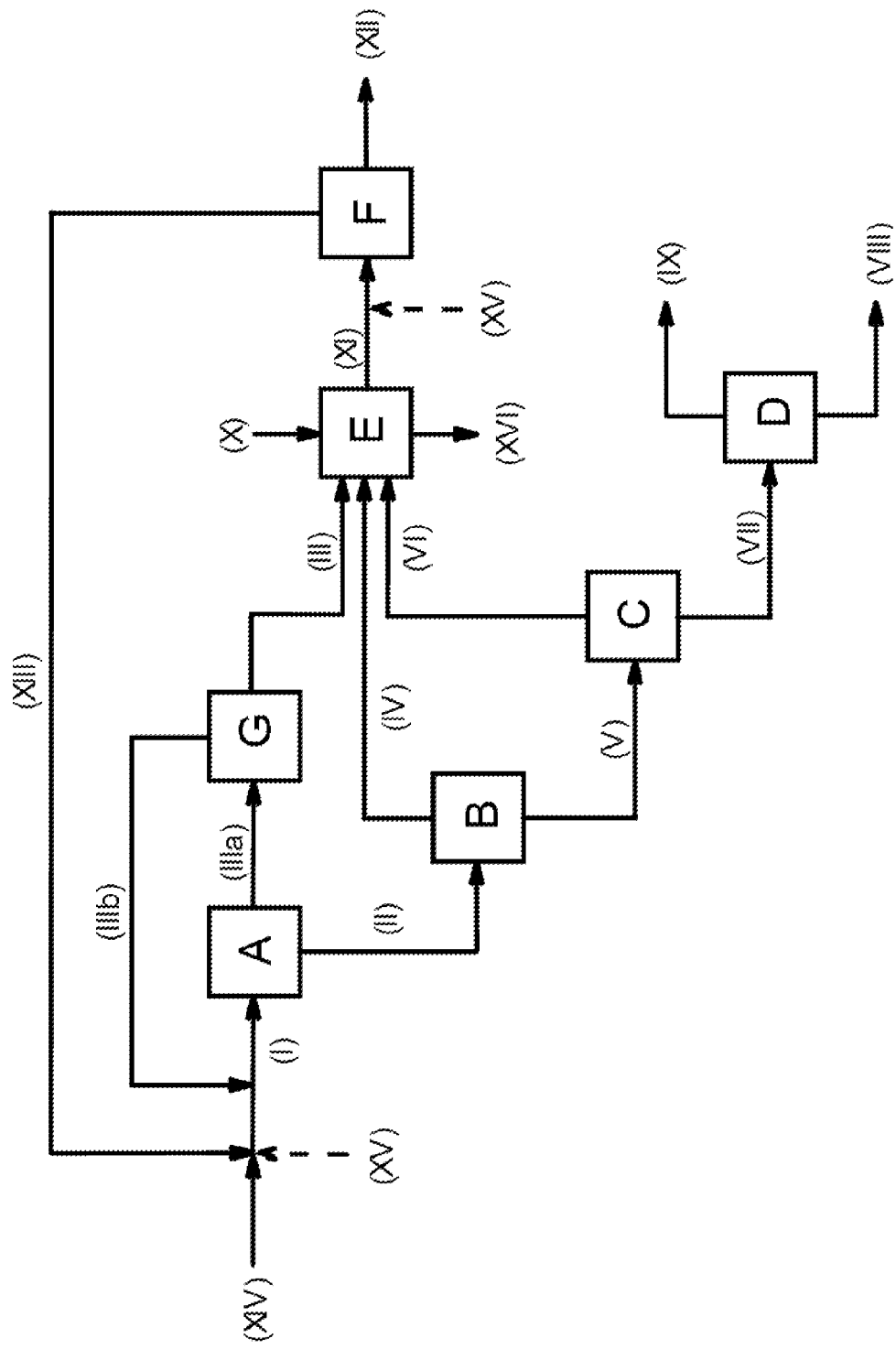
FIG. 3 shows a block diagram of a general embodiment in which hydrogen is separated off in a hydrogen recovery unit (G) and recycled.

In a preferred variant of the process of the invention, therefore, before stream (III) is fed to the combustion unit (E), hydrogen is separated off in a hydrogen recovery unit (G) and recycled to the methanol synthesis unit (A) of stage (a). FIG. 3 shows a block diagram of a general embodiment in which hydrogen is separated off in a hydrogen recovery unit (G) and recycled. In general, it is advantageous to feed the hydrogen separated off to the synthesis gas compressor in the methanol synthesis unit (A) and then to feed it into the reactor together with the compressed synthesis gas.

In principle, the hydrogen can be removed from stream (III) using any apparatuses suitable for separating hydrogen from a gas stream comprising carbon dioxide, carbon monoxide, hydrogen and methane. Corresponding apparatuses are common knowledge to the person skilled in the art, for example pressure swing adsorption or permeation. Preferably, in the process of the invention, the hydrogen is separated off in the hydrogen recovery unit (G) by pressure swing adsorption.

In pressure swing adsorption, the gas to be separated is guided into an adsorbent-filled vessel under elevated pressure, generally in the range from 0.6 to 1 MPa abs. The components heavier than hydrogen are adsorbed, and hydrogen as light component is conducted out of the vessel in concentrated form. If the adsorber bed has been largely saturated with the heavier components, the gas to be separated, for further adsorption, is guided into another, likewise adsorbent-filled vessel, and the heavier components are released again by desorption from the previous vessel by lowering the pressure and removed separately as such. In this way, the previous vessel is regenerated again and prepared for a new cycle.

Since a particularly high level of cost and inconvenience would be required to separate off the hydrogen completely, the separation is generally incomplete. Typically, when the hydrogen recovery unit (G) is used, only 50% to 95%, preferably ≥60% and preferably ≤90%, of the hydrogen present in the gas stream is removed. Therefore, stream (III), even after the separation of hydrogen, typically still comprises corresponding residual amounts of hydrogen.

The hydrogen separated off generally has a relatively high purity. The preferred pressure swing adsorption affords the hydrogen separated off generally in a purity of 90% to 100 vol.-%, preferably of ≥95 vol.-%, more preferably of ≥99 vol.-% and most preferably of ≥99.5 vol.-%.

In terms of energy, mass and the environment, it is preferred to increase the stoichiometric number S at the reactor inlet primarily first of all by utilizing the hydrogen present in the system via the hydrogen recovery unit (G) and to only supply the hydrogen feedstock (XIV) in an amount as required under the use of the hydrogen recovery unit (G). However, for example, in the event of an oversupply of hydrogen at the site of the methanol synthesis plant, it may be advantageous to dispense with the provision and operation of a hydrogen recovery unit.

Figure 1:
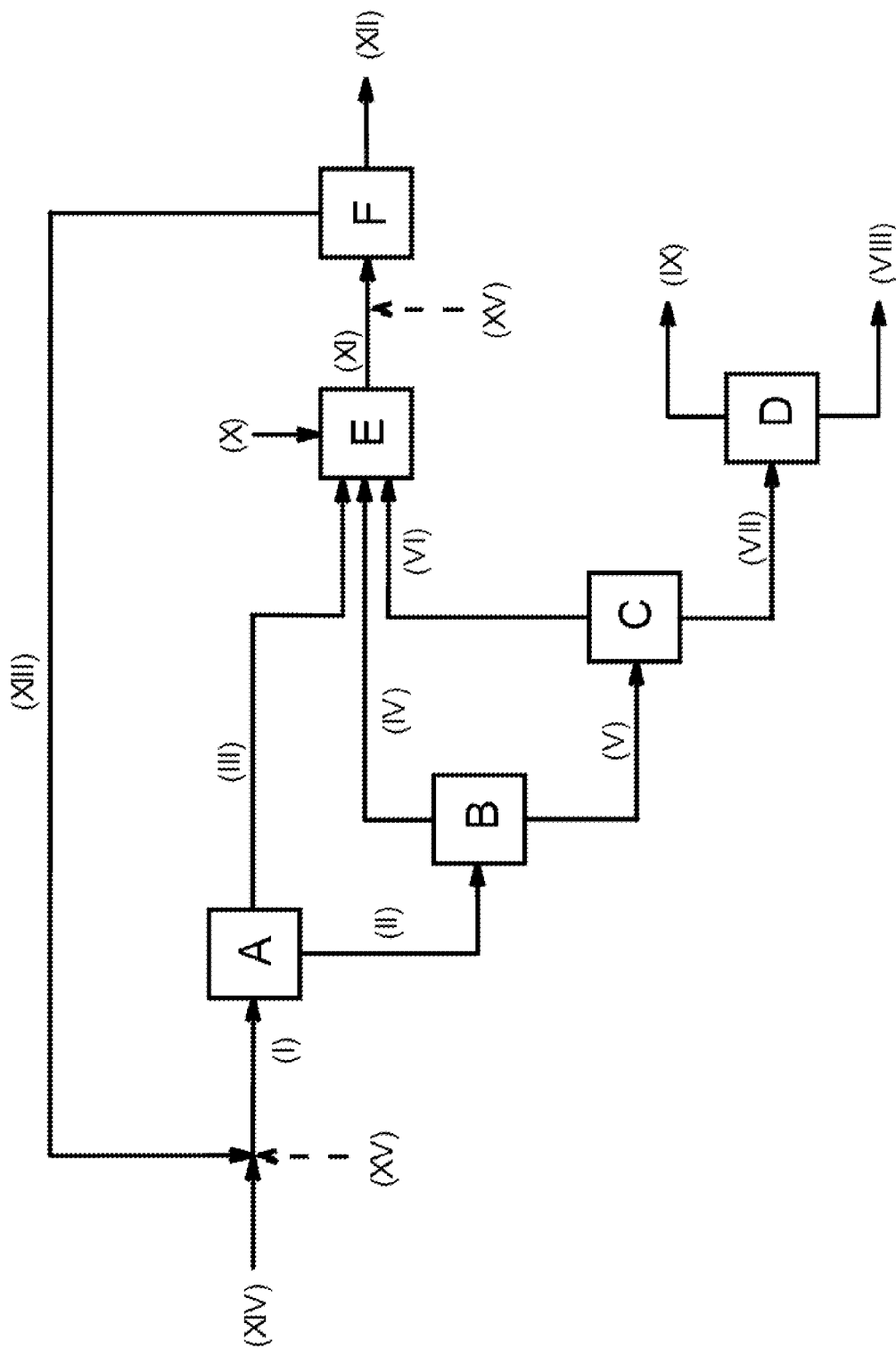
FIG. 1 shows the block diagram of a general embodiment of the process of the invention, in which all three streams (III), (IV) and (VI) are guided to combustion unit (E). The labels therein have the following meanings:
(A) methanol synthesis unit
(B) expansion unit
(C) low boiler distillation apparatus
(D) pure methanol distillation apparatus
(E) combustion unit
(F) carbon dioxide recovery unit
(I) carbon dioxide and hydrogen containing stream
(II) crude methanol stream
(III) gaseous stream comprising carbon dioxide, carbon monoxide, hydrogen and methane
(IV) expansion gas comprising carbon dioxide and methane
(V) degassed crude methanol stream
(VI) low boiler stream from distillation apparatus (C)
(VII) bottom stream from distillation apparatus (C)
(VIII) high boiler stream from distillation apparatus (D)
(IX) methanol
(X) oxygenous gas
(XI) flue gas
(XII) off-gas stream from carbon dioxide recovery unit (F)
(XIII) carbon dioxide-enriched stream from carbon dioxide recovery unit (F)
(XIV) hydrogen feedstock
(XV) carbon dioxide feedstock The dotted lines in stream (XV) indicate that stream (XV), according to the invention, can either be supplied to the carbon dioxide-containing flue gas (XI) or to the methanol synthesis unit (A) as a carbon dioxide containing source of stream (I).

The block diagram of a general embodiment of the process of the invention in which all three streams (III), (IV) and (VI) are guided to the combustion unit (E) is shown in FIG. 1. The general meanings of the apparatus units and apparatuses (A) to (F) and streams (I) to (XV) have already been listed in the general description of the invention with reference to FIG. 1.

The description which follows relates to a preferred embodiment with the following characteristics:

(A) The methanol synthesis unit (A) comprises a compressor for compression of the carbon dioxide and hydrogen containing stream (I), a methanol synthesis reactor comprising a methanol synthesis catalyst for conversion of the compressed carbon dioxide and hydrogen stream (I) to methanol, a condenser for condensing out crude methanol, and a corresponding conduit for recycling synthesis cycle gas. By condensation of the reaction mixture obtained, crude methanol (II) is obtained and conducted away. Uncondensed gas is conducted away as stream (III).

(B) The expansion unit (B) comprises a vessel in which the crude methanol (II) separated off is expanded, forming what is called expansion gas (IV) and degassed crude methanol (V).

(C) The degassed crude methanol (V) is worked up by distillation. In stage (c), for this purpose, low boilers (VI) are first removed, and methanol is further enriched in the bottom stream (VII). Distillation apparatus (C) is typically a distillation column, also called low boiler column.

(D) What is called the purifying distillation of the methanol is effected in distillation apparatus (D). For energy-related reasons, the use of what is called a two-pressure distillation is particularly advantageous here. Pure methanol is obtained as stream (IX), and high boilers are removed via the bottom as stream (VIII).

(E) The combustion unit (E) comprises a combustion chamber. The process streams (III), (IV) and (VI) separated off are guided into it and combusted with supply of an oxygenous gas (X) to give carbon dioxide. Owing to the advantages mentioned in the description, the use of pure oxygen as oxidizer is particularly preferred.

(F) In the carbon dioxide recovery unit (F), carbon dioxide is separated from the flue gas (XI) that has been removed from the combustion unit (E) and recycled via stream (XIII) to the methanol synthesis unit (A). The carbon dioxide recovery unit (F) is preferably what is called a carbon dioxide gas scrubbing unit, in which carbon dioxide is selectively scrubbed out in an absorber in an aqueous solution of an organic amine to form the off-gas stream (XII) and subsequently released again in a desorber.

(XIV) Hydrogen feedstock (XIV) is supplied from an external source to the methanol synthesis unit (A).

(XV) Carbon dioxide feedstock (XV) is supplied from an external source either to the flue gas stream (XI), or to the methanol synthesis unit (A), or supplied to both, depending on the concentration of the carbon dioxide in the carbon dioxide feedstock.

FIG. 2 is based on FIG. 1 and differs in that the combustion unit (E), as well as a combustion chamber, also comprises a condenser in which water is condensed out of the combustion gas and conducted away as stream (XVI). This distinctly reduces the water content in the flue gas (XI) by a relatively simple measure and facilitates the subsequent recovery of the carbon dioxide.

FIG. 3 is based on FIG. 2 and differs in that, before stream (III) is fed to the combustion unit (E), hydrogen is separated off in a hydrogen recovery unit (G). The hydrogen is preferably removed by pressure swing adsorption. The hydrogen removed is recycled as stream (IIIb) to the methanol synthesis unit (A) and preferably added to the compressor therein.

Figure 4:
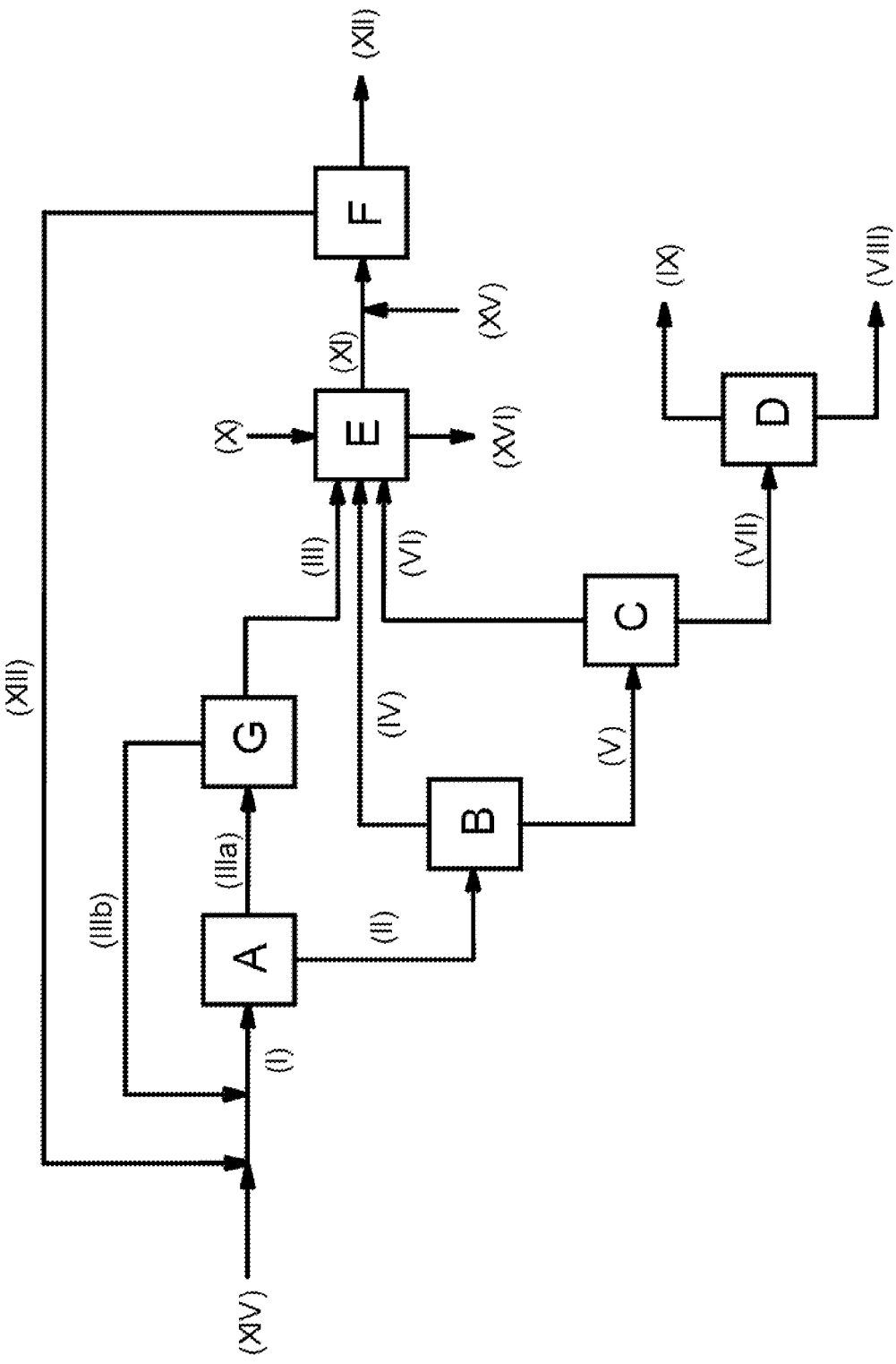
FIG. 4 shows a block diagram of a general embodiment.

FIG. 4 is based on FIG. 3 and differs in that the carbon dioxide feedstock (XV) is only supplied to the flue gas stream (XI).

Figure 5:
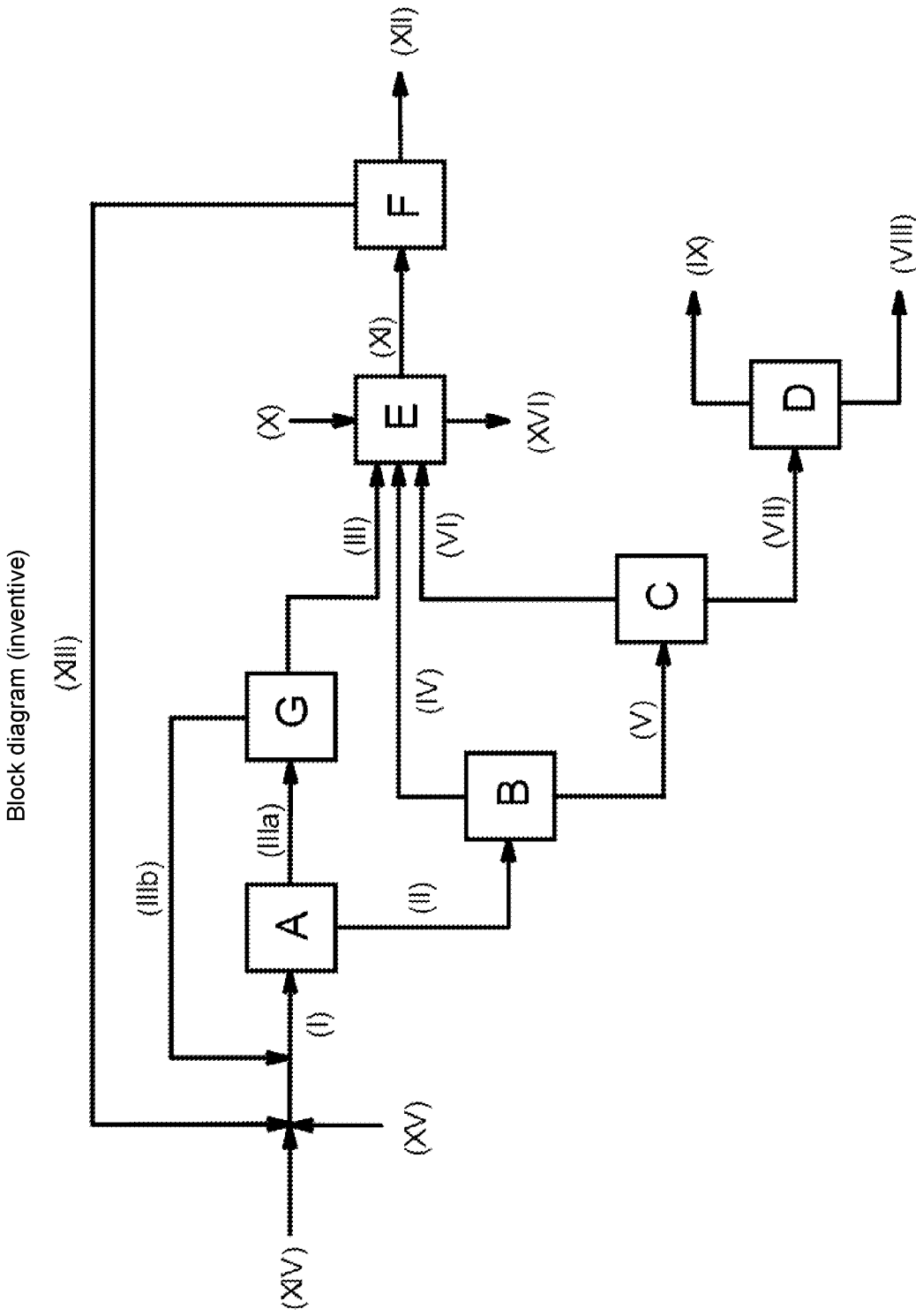
FIG. 5 shows a simplified block diagram of an interconnection for the inventive preparation of methanol.

FIG. 5 is based on FIG. 3 and differs in that the carbon dioxide feedstock (XV) is only supplied to the carbon dioxide-enriched stream (XIII).

The process of the invention enables the preparation of methanol from carbon dioxide and hydrogen in a high yield and purity using the apparatuses and interconnections that are customary in the methanol synthesis processes, but with the crucial advantage of a virtually complete physical utilization of the carbon-containing components of value for methanol synthesis and with avoidance of emission of carbon dioxide. However, the virtually complete physical utilization of the carbon-containing components of value for methanol synthesis not only avoids the emission of carbon dioxide which is harmful to the climate, but also increases the yield of methanol.

Owing to the use of the apparatuses and interconnections that are customary in the methanol synthesis process for the actual methanol synthesis and methanol workup, the process of the invention can also be retrofitted without difficulty in existing methanol synthesis plants. The apparatuses and process stages required for performance of the process of the invention, whether for retrofitting of existing methanol synthesis plants or the new construction of methanol synthesis plants, can be readily designed and installed by the person skilled in the art with common knowledge in the art. The cost and inconvenience associated with the installation and the operation of the components required is relatively low. The process of the invention at the same time also very elegantly solves the problem of the discharge of unwanted inert gases via the off-gas stream of the carbon dioxide recovery unit.

The process of the invention not only enables the virtually complete physical utilization of the carbon-containing components supplied as raw material and the avoidance of emission of carbon dioxide, but also the use of environmentally friendly raw materials. In contrast to synthesis gas, which is usually actively produced from natural gas or coal, carbon dioxide is often generated in many processes such as in power plants, waste incineration plants, steal and cement plants or various chemical plants as an unpleasant and unavoidable by-product or waste material, and is often easily available. The use of such carbon dioxide for the production of methanol avoids its release into the atmosphere and concurrently represents a climate-neutral manner to convert it into a valuable product. By the supply of hydrogen obtained in a climate-neutral manner, which has been obtained, for example, by electrolysis of water on the basis of solar, wind or water energy, it is additionally possible to further increase the sustainability of the process of the invention.

EXAMPLES

Interconnection 1 (Comparative Examples)

FIG. 6 shows a simplified block diagram of an interconnection for preparation of methanol according to the prior art. The labels therein have the following meanings:
(A) methanol synthesis unit
(B) expansion unit (low pressure expansion)
(C) low boiler column
(D) pure methanol column
(G) pressure swing adsorption
(I) carbon dioxide and hydrogen containing stream
(II) methanol- and water-enriched crude methanol
(IIIb) recovered hydrogen from pressure swing adsorption (G)
(III) off-gas from pressure swing adsorption (G)
(IV) expansion gas from expansion unit (B)
(V) degassed crude methanol stream
(VI) low boiler stream from low boiler column (C)
(VII) bottom stream from distillation apparatus (C)
(VIII) high boiler stream from pure methanol column (D)
(IX) pure methanol
(XIV) hydrogen feedstock ("fresh hydrogen")
(XV) carbon dioxide feedstock ("fresh carbon dioxide")

In addition, the interconnection has the following further features:
The methanol synthesis unit (A) comprises a synthesis cycle gas compressor, a reactor, a condenser and a synthesis cycle gas circuit.
The hydrogen recovery rate of the pressure swing adsorption (G) is 83%.

Unless stated otherwise in the respective comparative example, hydrogen is recovered via the pressure swing adsorption (G) and recycled via stream (IIIb) to the methanol synthesis unit (A), fresh hydrogen is supplied via stream (XIV) and fresh carbon dioxide via stream (XV). Streams (III), (IV) and (VI) are each discharged from the interconnection.

Interconnection 2 (Inventive Examples)

FIG. 5 shows a simplified block diagram of an interconnection for the inventive preparation of methanol. The labels therein have the following meanings:
(A) methanol synthesis unit
(B) expansion unit (low pressure expansion)
(C) low boiler column
(D) pure methanol column
(E) combustion unit
(F) carbon dioxide recovery unit
(G) pressure swing adsorption
(I) carbon dioxide and hydrogen containing stream (II) methanol- and water-enriched crude methanol
(IIIb) recovered hydrogen from pressure swing adsorption (G)
(III) off-gas from pressure swing adsorption (G)
(IV) expansion gas from expansion unit (B)
(V) degassed crude methanol stream
(VI) low boiler stream from low boiler column (C)
(VII) bottom stream from distillation apparatus (C)
(VIII) high boiler stream from pure methanol column (D)
(IX) pure methanol
(X) oxygenous gas
(XI) flue gas
(XII) off-gas from carbon dioxide recovery unit (F)
(XIII) carbon dioxide-enriched stream from carbon dioxide recovery unit (F)
(XIV) hydrogen feedstock ("fresh hydrogen")
(XV) carbon dioxide feedstock ("fresh carbon dioxide")
(XVI) condensed water from combustion unit (E)

In addition, the interconnection has the following further features:

The methanol synthesis unit (A) comprises a compressor, a reactor, a condenser and a synthesis gas circuit.

The combustion unit (E) comprises a combustion chamber and a condenser.

The combustible components are converted to carbon dioxide and water in the combustion chamber to an extent of >99%.

The carbon dioxide recovery rate of the carbon dioxide recovery unit (F) is >99%.

The hydrogen recovery rate of the pressure swing adsorption (G) is 83%.

Streams (III), (IV) and (VI) are combusted in the combustion unit (E) with supply of pure oxygen, and the flue gas (XI) obtained is supplied to the carbon dioxide recovery unit (F) for recovery of carbon dioxide. Recovered carbon dioxide is recycled as stream (XIII) to the methanol synthesis unit (A). The off-gas from the carbon dioxide recovery unit (F) is discharged from the interconnection.

Example 1

Comparative

Comparative example 1 relates to methanol synthesis from carbon dioxide and hydrogen. The underlying interconnection is shown in FIG. 6 and is described in detail as "interconnection 1". Table 1 shows the composition of the carbon dioxide feed stream (XV), which was 99.9 vol.-% of carbon dioxide and which corresponds to a typical composition for isolated carbon dioxide, and the composition of the hydrogen feed stream (XIV), which also was 99.9 vol.-% as a typical composition for hydrogen. The amounts of fresh carbon dioxide and fresh hydrogen fed into the synthesis unit as streams (XV) and (XIV) have been adjusted such that together with the recovered hydrogen (IIIb) from the pressure swing adsorption (G) and the methanol synthesis cycle gas loop inside of the methanol synthesis unit (A) a stoichiometric number S at the inlet of the methanol synthesis reactor of 3.40 was achieved. This relates to a stoichiometric number S of the streams fed to the methanol synthesis unit (A), which are the carbon dioxide feed stream (XV), the hydrogen feed stream (XIV) and the recovered hydrogen (IIIb) from the pressure swing adsorption (G), calculated as one combined stream, of 1.960. The stoichiometric number S of the mixture of the carbon dioxide feed stream (XV) and the hydrogen feed stream (XIV) was 1.869.

A stoichiometric number S of 1.960 at the inlet of the methanol synthesis is sufficient because of the high purge gas rate to assure a low inert component level in the methanol synthesis loop. Hence the amount of recovered hydrogen from the hydrogen recovery unit (G) is relatively high. A further reason is, that the carbon dioxide is much better soluble in the raw methanol coming from methanol synthesis the carbon monoxide. Hence it is removed out of the methanol synthesis loop and lost for the methanol synthesis. This causes an accumulation of the hydrogen in the methanol synthesis loop and lowers the hydrogen feedstock (XIV) amount necessary to adjust the stoichiometric demand.

The content of inerts ($CH_4$, $H_2O$, $N_2$) at the reactor inlet was only 6.7 vol.-%. A low inerts concentration is beneficial to assure a high conversion of the carbon dioxide to methanol, because the activity of the catalyst is lower for the conversion of carbon dioxide in comparison to standard carbon monoxide/carbon dioxide mixtures in conventional synthesis gases.

Conversion by heterogeneous catalysis over a copper-containing methanol synthesis catalyst at 210° C. and a pressure of 7.45 MPa abs and the further workup of the reaction mixture according to the simplified block diagram of FIG. 6 results in streams (III), (IV) (after expansion to 0.6 MPa abs at 40° C.) and (VI) with the amounts and compositions specified in table 1.

Owing to the discharge of streams (III), (IV) and (VI) from the interconnection, these remain unutilized for further methanol synthesis. In processes according to the prior art, these are typically supplied solely to a thermal utilization, i.e. not physically utilized. Thus, in the present comparative example 1,752 m$^3$ (STP) of carbon dioxide (XV) and 2158 m$^3$ (STP) of hydrogen are required for the preparation of one metric ton of pure methanol (stream (IX)).

Example 2

Inventive

Inventive example 2 likewise relates to methanol synthesis from carbon dioxide and hydrogen. The underlying interconnection is shown in FIG. 5 and is described in detail as "interconnection 2". Table 2 shows the composition of the carbon dioxide feed stream (XV), which was 99.9 vol.-% of carbon dioxide and which corresponds to a typical composition for isolated carbon dioxide, and the composition of the hydrogen feed stream (XIV), which also was 99.9 vol.-% as a typical composition for hydrogen, and which are identical to that from example 1. The amounts of fresh carbon dioxide and fresh hydrogen fed into the synthesis unit as streams (XV) and (XIV) have been adjusted such that together with the carbon dioxide-enriched stream (XIII) from the carbon dioxide recovery unit (F), the recovered hydrogen (IIIb) from the pressure swing adsorption (G) and the methanol synthesis recycle gas loop inside of the methanol synthesis unit (A) a stoichiometric number S at the inlet of the methanol synthesis reactor of 3.40 was achieved. This relates to a stoichiometric number S of the streams fed to the methanol synthesis unit (A), which are the carbon dioxide-enriched stream (XIII) from the carbon dioxide recovery unit (F), the carbon dioxide feed stream (XV), the hydrogen feed stream (XIV) and the recovered hydrogen (IIIb) from the pressure swing adsorption (G), calculated as one combined stream, of 1.957. The stoichiometric number S of the mixture of the carbon dioxide feed stream (XV) and the hydrogen feed stream (XIV) was 2.054.

The content of inerts ($CH_4$, $H_2O$, $N_2$) at the reactor inlet was only 7.1 vol.-%. A low inerts concentration is beneficial to assure a high conversion of the carbon dioxide to methanol, because the activity of the catalyst is lower for the conversion of carbon dioxide in comparison to standard carbon monoxide/carbon dioxide mixtures in conventional synthesis gases.

Conversion by heterogeneous catalysis over a copper-containing methanol synthesis catalyst at 210° C. and a pressure of 7.45 MPa abs and the further workup of the reaction mixture according to the simplified block diagram of FIG. 5 results in streams (III), (IV) (after expansion to 0.6 MPa abs at 40° C.) and (VI) with the amounts and compositions specified in table 2. By contrast with comparative example 1, however, these are not discharged unutilized from the interconnection, but combusted in accordance with the invention in the combustion unit (E) with supply of pure oxygen (X). After condensation of 94.2% of the water present and discharge thereof as stream (XVI), the carbon dioxide-containing flue gas (XI) is fed to a carbon dioxide recovery unit (F). >99% of the carbon dioxide present in the flue gas (XI) is isolated therein as stream (XIII) and recycled to the methanol synthesis unit (A).

Only 706 m³ (STP) of carbon monoxide (XV) are thus required for the preparation of one metric ton of pure methanol (stream (IX)) in inventive example 2.

By comparison with comparative example 1, in which streams (III), (IV) and (VI) are discharged unutilized from the interconnection, the process of the invention enables, in example 2, the substantial utilization of the carbon monoxide, carbon dioxide, methane and dimethyl ether components of value present in these streams for the further synthesis of methanol. The specific consumption of hydrogen remains unchanged because the composition of the recycled carbon dioxide is nearly similar to the carbon dioxide feed to the process. Specifically, it spares the use of 46 m³ (STP) of carbon dioxide (XV) per metric ton of pure methanol (stream (IX)).

TABLE 1

Data for example 1 (comparative)

| | Carbon dioxide (XV) | Hydrogen (XIV) | (IIIb) | (III) | (IV) | (VI) |
|---|---|---|---|---|---|---|
| Amount [m³ (STP)/t methanol] | 752 | 2158 | 68 | 45 | 10 | 12 |
| $CO_2$ [vol.-%] | 99.9 | 0 | 0 | 35.01 | 85.66 | 99.26 |
| $H_2$ [vol.-%] | 0 | 99.9 | 99.87 | 37.89 | 5.87 | 0.04 |
| CO [vol.-%] | 0 | 0 | 0 | 7.63 | 0.32 | 0 |
| $CH_3OH$ [vol.-%] | 0 | 0 | 0 | 0.64 | 3.18 | 0 |
| $CH_4$ [vol.-%] | 0 | 0 | 0.07 | 12.15 | 3.58 | 0.25 |
| $CH_3OCH_3$ [vol.-%] | 0 | 0 | 0 | 0.04 | 0.13 | 0.45 |
| $H_2O$ [vol.-%] | 0 | 0 | 0 | 0.13 | 0.73 | 0 |
| $N_2$ [vol.-%] | 0.1 | 0.1 | 0.07 | 6.44 | 0.29 | 0 |
| $O_2$ [vol.-%] | 0 | 0 | 0 | 0 | 0 | 0 |
| Ar [vol.-%] | 0 | 0 | 0 | 0 | 0 | 0 |
| Stoichiometric number S (XV) + (XIV) | 1.869 | | | | | |
| Stoichiometric number S (XV) + (XIV) + (IIIb) | | | 1.960 | | | |

TABLE 2

Data for example 2 (inventive)

| | Carbon dioxide (XV) | Hydrogen (XIV) | (IIIb) | (III) | (IV) | (VI) | (XI) | (XII) | (XIII) |
|---|---|---|---|---|---|---|---|---|---|
| Amount [m³ (STP)/t methanol] | 706 | 2156 | 64 | 42 | 10 | 12 | 52 | 6 | 45 |
| $CO_2$ [vol.-%] | 99.9 | 0 | 0 | 34.63 | 85.41 | 99.23 | 86.12 | 1.56 | 99.27 |
| $H_2$ [vol.-%] | 0 | 99.9 | 99.86 | 37.52 | 5.89 | 0.04 | 0 | 0 | 0 |
| CO [vol.-%] | 0 | 0 | 0 | 7.58 | 0.32 | 0 | 0 | 0 | 0 |
| $CH_3OH$ [vol.-%] | 0 | 0 | 0 | 0.64 | 3.18 | 0 | 0 | 0 | 0 |
| $CH_4$ [vol.-%] | 0 | 0 | 0.07 | 12.74 | 3.80 | 0.26 | 0 | 0 | 0 |
| $CH_3OCH_3$ [vol.-%] | 0 | 0 | 0 | 0.04 | 0.13 | 0.46 | 0 | 0 | 0 |
| $H_2O$ [vol.-%] | 0 | 0 | 0 | 0.13 | 0.73 | 0 | 3.32 | 3.00 | 0.73 |
| $N_2$ [vol.-%] | 0.1 | 0.1 | 0.07 | 6.66 | 0.30 | 0 | 5.96 | 53.89 | 0 |
| $O_2$ [vol.-%] | 0 | 0 | 0 | 0 | 0 | 0 | 4.50 | 40.68 | 0 |
| Ar [vol.-%] | 0 | 0 | 0 | 0 | 0 | 0 | 0.10 | 0.88 | 0 |
| Stoichiometric number S (XV) + (XIV) | 2.054 | | | | | | | | |
| Stoichiometric number S (XV) + (XIV) + (XIII) + (IIIb) | | | | 1.957 | | | | | |

The invention claimed is:

1. A process for preparing methanol by
   (a) converting a carbon dioxide and hydrogen containing stream (I) in a methanol synthesis unit (A) at a temperature of 150 to 300° C. and a pressure of 3 to 10 MPa abs in the presence of a methanol synthesis catalyst to a reaction mixture containing methanol, water, carbon dioxide, carbon monoxide, hydrogen, dimethyl ether and methane, condensing a methanol- and water-enriched crude methanol stream (II) out of said reaction mixture, and conducting the crude methanol stream (II) and a gaseous stream (III) comprising carbon dioxide, carbon monoxide, hydrogen and methane out of the methanol synthesis unit (A),
   (b) expanding the crude methanol stream (II) from stage (a) in an expansion unit (B) to a pressure of 0.1 to 2 MPa abs, and obtaining an expansion gas (IV) comprising carbon dioxide and methane and a degassed crude methanol stream (V) enriched with methanol and water,
   (c) separating a carbon dioxide- and dimethyl ether-comprising low boiler stream (VI) by distillation from the degassed crude methanol stream (V) from stage (b) in a distillation apparatus (C), and obtaining a methanol- and water-enriched bottom stream (VII), and
   (d) separating a water-containing high boiler stream (VIII) from the bottom stream (VII) from stage (c) in a further distillation apparatus (D), and obtaining methanol by distillation as stream (IX),
   which comprises
   (e) feeding the carbon dioxide, carbon monoxide, dimethyl ether and methane components of value in stream (III) and in at least one of the two streams (IV) and (VI) to a combustion unit (E) and combusting them therein with supply of an oxygenous gas (X) having an oxygen content of 30% to 100 vol.-%, forming carbon dioxide-containing flue gas (XI),
   (f) separating a carbon dioxide-enriched stream (XIII) from the carbon dioxide-containing flue gas (XI) from stage (e) in a carbon dioxide recovery unit (F) to form an off-gas stream (XII),
   (g) recycling the carbon dioxide-enriched stream (XIII) separated off in the carbon dioxide recovery unit (F) from stage (f) to the methanol synthesis unit (A) of stage (a) as a carbon dioxide containing source of stream (I),
   (h) supplying a hydrogen feedstock (XIV) to the methanol synthesis unit (A) of stage (a) as a hydrogen containing source of stream (I), and
   (i) supplying a carbon dioxide feedstock (XV) to the carbon dioxide-containing flue gas (XI) and/or to the methanol synthesis unit (A) of stage (a) as a carbon dioxide containing source of stream (I).

2. The process according to claim 1, wherein a copper- and zinc-containing heterogeneous catalyst is used as methanol synthesis catalyst in the methanol synthesis unit (A) in stage (a).

3. The process according to claim 1, wherein the methanol synthesis unit (A) in stage (a) comprises a compressor for compression of the carbon dioxide and hydrogen containing stream (I), a reactor for conversion of the compressed carbon dioxide and hydrogen containing stream (I), a condenser for condensing out the crude methanol stream (II), and a conduit for recycling of uncondensed gas to the reactor.

4. The process according to claim 1, wherein in stage (e), the carbon dioxide, carbon monoxide, dimethyl ether and methane components of value in streams (III), (IV) and (VI) are fed to the combustion unit (E).

5. The process according to claim 1, wherein the combustion unit (E) in stage (e) is supplied with an oxygenous gas (X) having an oxygen content of 90% to 100 vol.-%.

6. The process according to claim 1, wherein the combustion unit (E) in stage (e) comprises a combustion chamber and a condenser, water is condensed out of the combustion gas obtained in the combustion chamber in the condenser and conducted out of the combustion unit (E) as stream (XVI), and the remaining gaseous stream constitutes the carbon dioxide-containing flue gas (XI).

7. The process according to claim 1, wherein, in the carbon dioxide recovery unit (F) in stage (f), carbon dioxide is absorbed from the carbon dioxide-containing flue gas (XI) in an absorber in a basic solvent to form the off-gas stream (XII), the carbon dioxide-enriched stream (XIII) is released from the carbon dioxide-laden solvent in a desorber, and the carbon dioxide-depleted solvent is returned to the absorber.

8. The process according to claim 7, wherein the basic solvent used is an aqueous solution of an organic amine.

9. The process according to claim 8, wherein the organic amine used is monoethanolamine, piperazine, 2-amino-2-methyl-1-propanol, triethylenediamine, N-methyldiethanolamine or tert-butylaminoethoxyethanol.

10. The process according to claim 1, wherein the carbon dioxide-enriched stream (XIII) from stage (f) comprises oxygen, and stream (XIII), before it is recycled to the methanol synthesis unit (A), is catalytically hydrogenated to deplete the oxygen.

11. The process according to claim 1, wherein a carbon dioxide feedstock (XV) containing 5 to 95 vol.-% carbon dioxide based on the gaseous feedstock is supplied to the carbon dioxide-containing flue gas (XI).

12. The process according to claim 1, wherein a carbon dioxide feedstock (XV) containing 95 to 100 vol.-% carbon dioxide based on the gaseous feedstock is supplied to the methanol synthesis unit (A).

13. The process according to claim 1, wherein 50 to 100% of the carbon bound in the methanol (IX) is based on carbon dioxide supplied by the carbon dioxide feedstock (XV).

14. The process according to claim 1, wherein, before stream (III) is fed to the combustion unit (E), hydrogen is separated off in a hydrogen recovery unit (G) and recycled to the methanol synthesis unit (A) of stage (a).

15. The process according to claim 14, wherein the hydrogen is separated off by pressure swing adsorption in the hydrogen recovery unit (G).

* * * * *